US010215642B2

(12) United States Patent
Giakos

(10) Patent No.: US 10,215,642 B2
(45) Date of Patent: Feb. 26, 2019

(54) SYSTEM AND METHOD FOR POLARIMETRIC WAVELET FRACTAL DETECTION AND IMAGING

(71) Applicant: George C. Giakos, Fairlawn, OH (US)

(72) Inventor: George C. Giakos, Fairlawn, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 13/986,602

(22) Filed: May 17, 2013

(65) Prior Publication Data

US 2013/0308132 A1 Nov. 21, 2013

Related U.S. Application Data

(60) Provisional application No. 61/648,280, filed on May 17, 2012.

(51) Int. Cl.
*G01J 4/04* (2006.01)
*G01N 21/23* (2006.01)

(52) U.S. Cl.
CPC .............. *G01J 4/04* (2013.01); *G01N 21/23* (2013.01)

(58) Field of Classification Search
CPC ........ G01J 4/04; G01J 4/00; G01J 3/02; G01J 3/0224; G01N 21/211; G01N 21/21; G01N 33/6893; G01N 21/6486
USPC ........ 356/369, 364, 367, 445, 342; 250/225, 250/559.09

See application file for complete search history.

(56) References Cited

U.S. PATENT DOCUMENTS

| | | | | |
|---|---|---|---|---|
| 5,788,632 | A * | 8/1998 | Pezzaniti et al. | 600/316 |
| 5,995,228 | A * | 11/1999 | Otani | G01J 4/00 356/364 |
| 6,373,614 | B1 * | 4/2002 | Miller | G01J 1/26 250/201.1 |
| 6,961,123 | B1 * | 11/2005 | Wang et al. | 356/364 |

(Continued)

OTHER PUBLICATIONS

Noodeh et al., "Application of wavelets and fractal-based methods for detection of Microcalcification in Mammograms, A Comparative Analysis using Neural Network"; International Conference on Graphic and Image Processing (ICGIP 2011), SPIE—2011.*

(Continued)

*Primary Examiner* — Mohamed K Amara
(74) *Attorney, Agent, or Firm* — Renner Kenner Greive Bobak Taylor and Weber; Timothy A. Hodgkiss; Ray L. Weber

(57) ABSTRACT

A system and method for detection of a target object/material includes identifying a polarimetric signal for a plurality of aspect angles. One/two-dimensional Mueller matrix image or one/two-dimensional Stokes vector image can be processed using power spectral analysis, wavelet and fractal analysis for further image, having increased discrimination with reduced false-ratio. In addition, each of the angular polarization states due to their association with a particular aspect angle are then cross-correlated to generate a two-dimensional image that relates the level of correlation with the aspect angle. Finally, the output information, including statistical parameters are fed to the input of a neural-fuzzy network for further optimization and image enhancement.

13 Claims, 20 Drawing Sheets

(56) References Cited

U.S. PATENT DOCUMENTS

| | | | | |
|---|---|---|---|---|
| 7,761,139 B2* | 7/2010 | Tearney | A61B 5/0066 | 600/473 |
| 7,865,231 B2* | 1/2011 | Tearney | A61B 1/00165 | 600/407 |
| 9,554,738 B1* | 1/2017 | Gulati | A61B 5/1455 | |
| 9,610,018 B2* | 4/2017 | Gulati | A61B 5/02416 | |
| 2002/0126277 A1* | 9/2002 | Norton | G01J 3/02 | 356/326 |
| 2005/0264813 A1* | 12/2005 | Giakos | | 356/369 |
| 2006/0164652 A1* | 7/2006 | Cyr | G01J 4/04 | 356/477 |
| 2006/0187451 A1* | 8/2006 | McIntyre | G01J 4/04 | 356/364 |
| 2006/0215159 A1* | 9/2006 | Smith | | 356/367 |
| 2007/0146632 A1* | 6/2007 | Chipman | | 351/205 |
| 2008/0062407 A1* | 3/2008 | Boroditsky | H04B 10/85 | 356/73.1 |
| 2009/0028423 A1* | 1/2009 | Sandstrom et al. | | 382/149 |
| 2009/0119808 A1* | 5/2009 | Giakos | | 850/31 |
| 2009/0247862 A1* | 10/2009 | Meyer | A61B 3/102 | 600/425 |
| 2009/0296089 A1* | 12/2009 | Smith | | 356/367 |
| 2010/0045956 A1* | 2/2010 | Van De Kerkhof | G01M 11/0264 | 355/71 |
| 2011/0285982 A1* | 11/2011 | Breed | | 356/4.01 |
| 2012/0078099 A1* | 3/2012 | Suri | A61B 8/483 | 600/440 |
| 2012/0182542 A1* | 7/2012 | Walsh | G03F 7/0002 | 356/51 |
| 2012/0212742 A1* | 8/2012 | Lo | G01J 4/04 | 356/364 |
| 2014/0043609 A1* | 2/2014 | Baba | G01N 21/51 | 356/366 |
| 2014/0063299 A1* | 3/2014 | Fest | H04N 5/2254 | 348/273 |
| 2014/0175261 A1* | 6/2014 | Addison | A61B 5/7221 | 250/206 |
| 2014/0314332 A1* | 10/2014 | Mudge | G01J 4/04 | 382/255 |
| 2015/0100277 A1* | 4/2015 | Smith et al. | | 702/189 |
| 2015/0219497 A1* | 8/2015 | Johs | G01J 4/02 | 356/367 |
| 2015/0219498 A1* | 8/2015 | Tillotson | G01J 4/04 | 348/144 |
| 2016/0116397 A1* | 4/2016 | Freudenthal | G01N 21/23 | 356/370 |
| 2017/0003271 A1* | 1/2017 | Nadkarmi | G01N 11/00 | |
| 2017/0102319 A1* | 4/2017 | De Martino | G01N 21/21 | |

OTHER PUBLICATIONS http://www.mathworks.com/help/wavelet/examples/wavelet-scalogram-using-1d-wavelet-analysis.html (Sep. 4, 2009).*
https://en.wikipedia.org/wiki/Scaleogram.*
https://en.wikipedia.org/wiki/Mueller_calculus.*
"Light Scattering Reviews 4" By A. Kokhanovsky, Ed. Springer (2009) (see pp. xxiv, 12-13, 71-73 for ex.).*

* cited by examiner

SYSTEM AND METHOD FOR POLARIMETRIC WAVELET FRACTAL DETECTION AND IMAGING

CROSS-REFERENCE TO RELATED APPLICATION

This application claims the benefit of U.S. Provisional Application No. 61/648,280 filed on May 17, 2012, the contents of which are incorporated herein by reference.

STATEMENT REGARDING FEDERALLY-SPONSORED RESEARCH OR DEVELOPMENT

This invention was made with government support under Contract No. FA8718-09-C-0040 awarded by the U.S. Air Force Research Laboratory. The government has certain rights in the invention.

TECHNICAL FIELD

Generally, the present invention relates to a system and method of polarimetric wavelet fractal detection and imaging of a target object/material. Particularly, the present invention relates to a system and method of polarimetric wavelet fractal detection and imaging at different aspect angles to achieve enhanced detection and discrimination of the backscattered or transmission characteristics of a target object/material. More particularly, the present invention relates to a system and method for both remote and microscopic detection and imaging of a target object/material using a combined cross-correlation, power spectral density (PSD), fractal and wavelet analysis of polarimetric signals at different aspect angles to enable detection of the target object/material with enhanced discrimination, localization, and high dynamic range.

BACKGROUND ART

Digital imaging is a process used to recognize objects of interest in an image by utilizing electronic sensors and advanced computing techniques with the aim of improving image quality parameters. Furthermore, digital imaging is intrinsically difficult due to the fact that image formation is basically a many-to-one-mapping (i.e. characterization of three-dimensional (3-d) objects can be deduced from either a single image or multiple images). In addition, several problems associated with low-contrast images, including: blurred images, noisy images, image conversion to digital form, transmission, handling, manipulation, and storage of large-volume images, have led to the development of efficient image processing and recognition algorithms. Specifically, digital imaging or computer vision involves image processing and pattern recognition techniques, whereby image processing techniques utilize image enhancement, manipulation, and analysis of images, and pattern recognition utilizes object identification from observed patterns and images. Recently, significant advances have been made in pattern recognition, through the use of several new types of computer architectures that utilize very large-scale integrated circuits (VLSI) and solid state memories with a variety of parallel high-speed computers, optical and opto-digital computers, as well as a variety of neural network architectures and implementations. Artificial neural networks (ANN) have shown to be highly capable in solving problems that are not governed by rules, or in which traditional techniques have failed or proved inadequate. The inherent parallel architecture and the fault tolerant nature of the artificial neural networks is maximally utilized to address problems in a variety of application areas related to the field of imaging. Artificial neural networks (ANN) find their application in pattern recognition (classification, clustering, feature selection), texture analysis, segmentation, image compression, color representation and several other aspects of image processing, with applications in medical imaging, remote sensing, aerospace, radars, and military applications.

Wavelets are a family of transforms whose basis functions are of short duration and finite energy. In contrast to the Fourier transform, which effectively assumes that a signal is stationary at time scales of interest, the wavelet transform determines a signal's frequency content as a function of time. Thus, the use of Fourier or wave transforms results in a trade-off between localization in the time and frequency domains. Specifically, the time and frequency domain analysis provided by the wavelet transform provides the opportunity to explore the nature of transient signals by representing the time varying spectral response through time-frequency maps, as well as to analyze signals for conditions where responses change significantly in amplitude during experiments. As such, wavelets have found application in situations that require analysis over a very short time duration or where information is localized.

Fractal geometry is the geometry of self-similarity in which objects appear to look similar at different scales. The key concept of fractal analysis relies on the fact that a fractal dimension can be considered as a quantitative measure of object surface heterogeneity because of its inherent self-similarity features. The fractal dimension can be interpreted as a measure of heterogeneity of a set of points on a plane, or in space, for instance, a measure of surface roughness.

Combining both techniques of wavelet and fractal analysis allows enhanced detection, discrimination, tracking and identification of objects to be achieved, however such techniques have yet to be utilized in imaging of polarimetric signals.

The physical algorithm and applied metrics of this study on the material characterization of space materials is shown in FIG. 1, with reference to polysilicon, a material found to exhibit higher diffused scattering characteristics, depolarization, and fractal dimension, with respect to amorphous silicon.

Polarimetric imaging of target objects/materials offers unique advantages for a wide range of detection and classification problems due to the intrinsic potential for high contrast in different polarization components of backscattered light that is detected from the target object/material during its imaging. Moreover, polarimetric imaging can yield high-specificity images of the target object/material in high-dynamic range and extreme condition scenarios, such as in scattering media, or cluttered environments, while at the same time acquiring information related to the material composition and the surface characteristics of the target object/material.

While polarimetric imaging provides the various advantages discussed above, there is still a need for further enhancement in target object/material detection, tracking, discrimination, and identification.

Therefore, there is a need for a system and method for polarimetric wavelet detection that is able to achieve enhanced detection of a target object/material, such as space materials. In addition, there is a need for a system and method for polarimetric wavelet detection that is able to remotely characterize a target object/material, such as space materials, with enhanced discrimination, localization, and high-dynamic range, and high sensitivity. Furthermore, there is a need for a system and method for polarimetric wavelet detection that combines cross-correlation and wavelet principles with polarimetric imaging at different aspect angles to achieve enhanced detection and characterization of a target object/material.

SUMMARY OF THE INVENTION

In light of the foregoing, it is a first aspect of the present invention to provide a system and method for polarimetric wavelet fractal detection and imaging that provides enhanced signal detection, tracking, discrimination, and identification by applying wavelet and fractal analysis.

In another aspect of the present invention a method for imaging a target object comprises providing an illumination source to illuminate the target object over a plurality of aspect angles; collecting the backscattered or transmitted light from the target object over the plurality of aspect angles at a detector, said backscattered or transmitted light defining a one or two-dimensional polarimetric state signal for each one of said plurality of aspect angles; generating, at a computer in communication with said detector, a Mueller Matrix image, said Mueller Matrix image having a plurality of elements associated with each said aspect angle; computing at said computer a cross-correlation of the polarimetric state signals for each said aspect angle; and displaying a two-dimensional image based on said cross-correlation of said polarimetric signals and said aspect angles to characterize the target object.

Still another aspect of the present invention is to provide method for imaging a target object that comprises providing an illumination source to illuminate the target object over a plurality of aspect angles; collecting the backscattered or transmitted light from the target object over the plurality of aspect angles at a detector, said backscattered or transmitted light defining a one or two-dimensional polarimetric signal for each one of said plurality of aspect angles; generating at a computer in communication with said detector a Stokes vector image with each said aspect angle; computing at said computer the cross-correlation of the polarimetric signals for each said aspect angle; and displaying a two-dimensional image based on said cross-correlation of said polarimetric signals and said aspect angles to characterize the target object.

Another aspect of the present invention is to provide a system for imaging a target object that comprises an illumination source configured to generate a light beam to illuminate the target object; a detector to detect the backscatted images from the target object; and a controller coupled to said illumination source and said detector; wherein said light beam is moved through different aspect angles relative to the target object, such that said detector collects images defined by said backscattered light beam, so as to define a one or two-dimensional polarimetric signal for each one of said plurality of said aspect angles, whereupon said controller computes a cross-correlation of the polarimetric state signals for each said aspect angle to image the target object.

BRIEF DESCRIPTION OF THE DRAWINGS

These and other features and advantages of the present invention will become better understood with regard to the following description, appended claims, and accompanying drawings wherein:

DETAILED DESCRIPTION OF THE INVENTION

Figure 1:
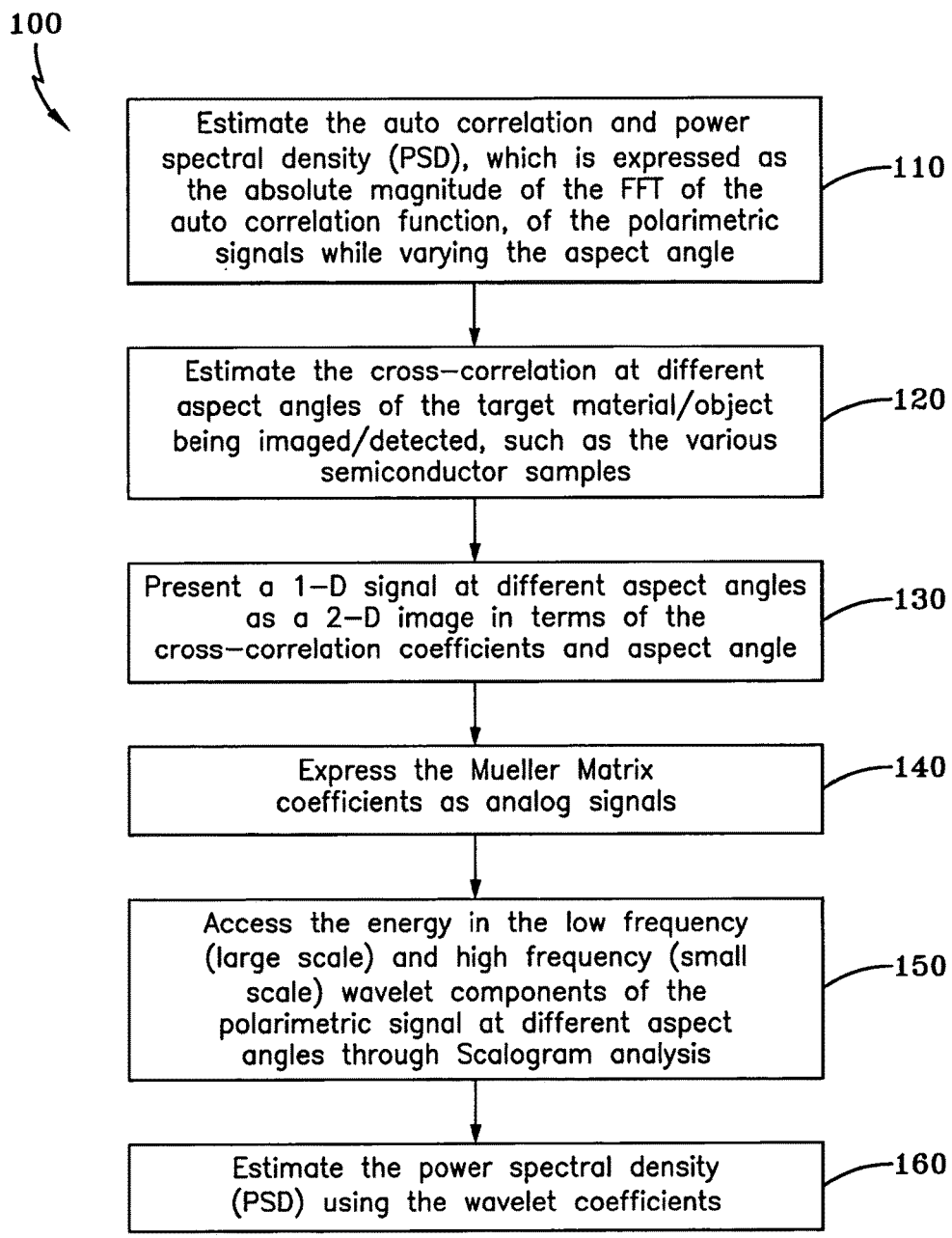
FIG. 1 is a flow diagram showing the operational steps taken by the polarimetric wavelet detection system and method in accordance with the concepts of the present invention.

Typically, a Mueller Matrix representing the backscattered image of a target object/material is defined by Mueller Matrix coefficients that are expressed in Cartesian coordinates $m_{ij}(x,y)$. However, the present invention is configured such that the Mueller Matrix of a target object/material, such as the amorphous, polysilicon semiconductor samples discussed below, is expressed as a function of aspect angle, $\theta$, whereby:

$$M(\theta) = \begin{bmatrix} m_{00}(\theta) & m_{01}(\theta) & m_{02}(\theta) & m_{03}(\theta) \\ m_{10}(\theta) & m_{11}(\theta) & m_{12}(\theta) & m_{13}(\theta) \\ m_{20}(\theta) & m_{21}(\theta) & m_{22}(\theta) & m_{23}(\theta) \\ m_{30}(\theta) & m_{30}(\theta) & m_{32}(\theta) & m_{33}(\theta) \end{bmatrix} \quad (1)$$

That is, the angle $\theta$ is the aspect angle of the target object/material being imaged or otherwise being detected. As such, the present invention is configured, so that the Mueller Matrix elements, as well as the Mueller Matrix decomposition, are expressed as a function of the aspect angle of the target object/material relative to the laser beam used to generate the backscattered signals detected by the photo detector used by the polarimetric detection system. As a result, an angular Mueller Matrix description of the target object/material, and a corresponding wavelet analysis, is achieved. It should be appreciated that the target or target object/material may include any target object or material that is desired to be detected using the present invention discussed herein.

Each polarimetric state, as provided by the present invention, can be expressed in terms of wavelets, whereby:

$$m_{ij}(t, \theta) = \Sigma_{a,b} c_{ab} \psi_{ab}(t, \theta) \quad (2)$$

where $\psi_{ab}(t, \theta)$ are shifted and scaled versions of the mother wavelet function, which is dilated and translated by factors $a$ and $b$, respectively to yield:

$$\psi_{ab}(t, \vartheta) = \frac{1}{\sqrt{|a|}} \psi\left(\frac{t-b}{a}, \theta\right). \quad (3)$$

The continuous wavelet transform is given by:

$$W_{\psi\backslash m} m_{ij}(\theta)(a, b) = \frac{1}{\sqrt{|a|^{1/2}}} \int_{-\infty}^{+\infty} \psi^*\left(\frac{t-b}{a}\right) m_{ij}(t, \theta) dt \quad (4)$$

where $\psi^*$ is the complex conjugate of the analyzing wavelet, also known as the kernel wavelet, and the coefficients are given by:

$$c_{ab} = W_{\psi\backslash m} m_{ij}(\theta)(a, b) \quad (5)$$

The 16 polarimetric states can be analyzed using continuous wavelet transforms (CWTs) and their respective scalograms can be plotted.

Similarly, wavelet transform and fractal analysis can and be applied to process the angular Mueller Matrix and its decomposition matrices as a function of the aspect angle as well as its decomposition matrices. Furthermore, the Mueller Matrix is able to be decomposed in terms of the depolarization, retardance, and diattenuation components as a function of the aspect angle $\theta$, whereby $$M(\theta) = M_{depol}(\theta) M_{ret}(\theta) M_{diat}(\theta) \quad (6).$$

As such, $M_{depol}(\theta)$ accounts for the depolarizing effects of the medium, $M_{ret}(\theta)$ accounts for the linear birefringence and optical activity, and $M_{diat}(\theta)$ describes the effects of linear and circular dichroism. From these matrices, the diattenuation, retardance, and depolarization characteristics of the medium are readily determined.

The depolarization is quantified in terms of the depolarization index, $P_D$ according to $$P_D(\theta) = Dep(M(\theta)) = 1 - \frac{\sqrt{((\Sigma_{i,j} m_{ij}^2(\theta)) - m_{00}^2(\theta)}}{\sqrt{3} \, m_{00}^2(\theta)} \quad (7)$$

where $m_{ij}(\theta)$ are the angular Mueller Matrix elements as a function of the aspect angle.

From the decomposed retardance matrix, $M_{ret}(\theta)$, the total retardance, R, which includes the effects of both linear and circular birefringence, can be expressed as $$R(\theta) \cos^{-1}\left(\frac{tr(M_{ret}(\theta))}{2} - 1\right) \quad (8)$$

where $tr(M_{ret}(\theta))$ is the trace of the retardance matrix.

The diattenuation, d, is dependent of the first row vector of the angular Mueller Matrix. This vector describes differential attenuation for both linear and circular polarization states and can be expressed as $$d(\theta) = \frac{1}{m_{00}(\theta)} \times \sqrt{m_{01}^2(\theta) + m_{02}^2(\theta) + m_{03}^2(\theta)}. \quad (9)$$

It should be appreciated that the computation of the angular Mueller Matrix $M(\theta)$, which is based on the aspect angle of the target object/material being imaged or detected, as well as the expression of the Mueller Matrix coefficients in wavelet form may be carried out using any suitable computing system, such as a portable computing device or FPGA (field programmable gate array), for example.

The wavelet expression of the polarization state signals allow the cross-correlation of detected polarimetric signals based on aspect angle of the target object/material. This correlation enables enhanced detection and discrimination of the target object/material in a manner to be discussed.

By applying the data reduction technique, the calibration matrix can be determined that permits the calculation of the four Stokes parameters, given a 4-frames raw vector.

Specifically, the states of polarization of a target can be characterized through its four Stokes parameters ($S_0$, $S_1$, $S_2$, and $S_3$). These Stokes parameters can be written as a column matrix form, referred to as a Stokes vector, according to:

$$S = \begin{pmatrix} S_0 \\ S_1 \\ S_2 \\ S_3 \end{pmatrix} \quad (10)$$

For a partially polarized light, the total light intensity, $S_0$, is offered in terms of the three polarization states $S_1$, $S_2$, and $S_3$ as:

$$S_0^2 \geq S_1^2 + S_2^2 + S_3^2 \quad (11).$$

The Stokes vector $\bar{S}_{out}$, at the input of the detector, is related to the incident Stokes vector $\bar{s}_{in}$ through the Muller matrix A, where A describes the elements of the analyzer polarization of the phase retarder and the polarizer in front of the detector, including instrumental polarization, and polarization sensitivity of the detector; the polarimetric system acquires n-optical polarimetric images at different aspect angle of the target object/material, that are obtained through optical illumination of the target object/material, active or passive, of the target object/material. Subsequent calculations are performed on each pixel of a target scene by measuring all four components of the Stokes vector.

Specifically, the Stokes vector incident on the detector is:

$$\bar{S} = A\bar{S}_{inc} \quad (12)$$

where $\bar{S}_{inc} = (s_0\ s_1\ s_2\ s_3)^T$ is the Stokes vector incident on the polarization state analyzer and A is the Mueller matrix that describes both the elements of the polarization state analyzer and instrumental polarization between the polarization state analyzer and the detector. An analyzer vector $\bar{A} = (a_0\ a_1\ a_2\ a_3)$ analogous to the Stokes vector can be constructed. The output at the detector I is proportional to the incident intensity and is found by the dot product:

$$i = \bar{A} \cdot \bar{S}_{inc} = a_0 s_0 + a_1 s_1 + a_2 s_2 + a_3 s_3. \quad (13)$$

The incident Stokes vector $\bar{S}_{inc}$ is determined by making a series of measurements $i_q$, changing the elements of the polarization state analyzer for each measurement. The intensity of the $q^{th}$ measurement is:

$$i_1 \bar{A}_q \cdot \bar{S}_{inc} \quad (14)$$

where $\bar{A}_q$ is the analyzer vector for the $q^{th}$ measurement. The expression for Q measurements is conveniently expressed as:

$$\begin{pmatrix} i_0 \\ i_1 \\ \vdots \\ \vdots \\ i_{Q-1} \end{pmatrix} = \begin{pmatrix} a_{00} & a_{01} & a_{02} & a_{03} \\ a_{10} & a_{11} & a_{12} & a_{13} \\ \vdots & & & \\ \vdots & & & \\ a_{(Q-1)0} & a_{(Q-1)1} & a_{(Q-1)2} & a_{(Q-1)3} \end{pmatrix} \begin{pmatrix} S_0 \\ S_1 \\ S_2 \\ S_3 \end{pmatrix} \quad (15)$$

where $a_{qj}$ is the $j^{th}$ (j=0,1,2,3) element of $\bar{A}_q$ for the $q^{th}$ measurement. This is rewritten as:

$$\bar{I}_q = W\bar{S}_{inc} \quad (16)$$

where W is the polarimetric measurement matrix.

If the polarimetric measurement matrix is known, the calculated Stokes vector $\bar{R}$ can be found from the inverse of that matrix and the measured intensities by the polarimetric data reduction equation according to:

$$\bar{R} = W^{-1}\bar{I} + U\bar{I} \quad (17)$$

where U is the polarimetric data reduction matrix. For more than four measurements, W is not square and the pseudo-inverse is used. If the retarder is a quarter-wave retarder, the Mueller calculus equation is:

$$\bar{S} = M_p M_r(\theta_q)\bar{S}_{inc} \quad (18).$$

Therefore, the Stokes vector images can be constructed in addition to the degree of linear polarization (DOLP), the degree of polarization (DOP), degree of circular polarization (DOCP), ellipticity, e and orientation, η, all images, related in terms of Stokes parameters as:

$$DOLP = \frac{(S_1^2 + S_2^2)^{1/2}}{S_0} \quad (19)$$

$$DOP = \frac{(S_1^2 + S_2^2 + S_3^2)^{1/2}}{S_0} \quad (20)$$

$$DOCP = \frac{S_3}{S_0} \quad (21)$$

$$e = \frac{b}{a} = \frac{s_3}{s_0 + \sqrt{s_1^2 + s_2^2}} \quad (22)$$

$$\eta = \frac{1}{2}\arctan\left[\frac{s_2}{s_1}\right] \quad (23)$$

Fractal wavelet analysis can be applied to one-dimensional (1-d) imaging signals or two-dimensional (2-d) full images for further enhancement of the detection and discrimination capabilities. The polarimetric fractal wavelet analysis can be expanded on the Mueller matrix images and their decomposed images (diattenuation, retardance, depolarization), as well as entropy images for further detection enhancement under transmission, or backscattered geometry.

The polarimetric fractal wavelet analysis can be expanded on the Stokes vector images, DOP, DOL, DOCP, eccentricity, and ellipticity images for further detection enhancement under transmission, or backscattered illumination. Adaptive power spectral analysis of polarimetric imaging signals can provide further image enhancement and discrimination.

Thus, fractal and wavelet parameters, together with statistical parameters feeding a neural network can be used to optimize synergistically, the detection, tracking, and discrimination process.

Moreover, the signals obtained in this study are one-dimensional (1-d) polarimetric signals and hence a fractal dimension applicable to one-dimensional signals must be applied. There are several methods for computation of fractal dimension, such as the "Box Counting Method," the "Multiresolution Box-counting Method," the "Katz Method," the "Sevcik Method," the "Higuhi Method," the "Regularization Method," the "Maximum Entropy Method," and others. Typically, the box counting method is based on the method of covering the part, whose fractal dimension is to be calculated, with a number of square boxes and hence the number of boxes N(r) of size r is calculated which is required to cover the part. As the size of the square r (side of a square) approaches zero, the area covered by the square boxes will converge to a measure of the curve which can be expressed mathematically as:

$$D_B = \lim_{r \to 0}(\log(N(r))/\log(1/r)). \quad (24)$$

In practice, the fractal dimension is calculated by fitting the log-log plot of log(N(r)) versus log(1/r) (least squares method) and then calculating the slope of the plot. The slope of the plot gives the fractal dimension of the signal, which gives $$\log(N(r)) = D_B \log(1/r) + C \quad (25).$$

Here, $D_B$ is the fractal dimension or box counting fractal dimension of the signal. The method requires 2-D processing of the curve at various grid sizes, which increases the computational time. Similarly, The power spectral density function (i.e. the Fourier Transform of the auto-correlation function) can be used.

The wavelet fractal technique of the present invention applies to any polarimetric system capable of producing Mueller matrix images and Stokes vectors images regardless of the source of illumination. Specifically, the operational steps associated with carrying out the present invention, are generally referred to by numeral 100 set forth in FIG. 1. As previously discussed, the operational steps 100 of the present invention may be carried out by any suitable computer system that is capable of receiving information input thereto and that is capable of outputting the processed data in visual form. Initially, at step 110 of the process 100, quasi-monostatic backscattered polarimetric imaging is conducted on any suitable target object/material, such as amorphous silicon and polysilicon panel samples, using any suitable laser source and detector, which will be discussed in detail below. In particular the imaging includes modeling and calibrating a polarimeter, such as a 1060 nm liquid crystal NIR (near infrared) polarimeter for example; and recording of backscattered polarimetric signal intensities backscattered from the target object/material as a function of the various aspect angles of the target object/material. At step 110, the process 100 estimates the autocorrelation and power spectral density (PSD) of the polarimetric signals over various aspect angles of the target object/material being imaged. In particular, the autocorrelation and power spectral density (PSD) values of the imaged target object/material are expressed as the absolute magnitude of the Fast Fourier Transform (FFT) of the autocorrelation function.

Next, at step 120, the computed cross-correlation is estimated by the computer system at different aspect angles of the target object/material. Once estimated, the process continues to step 130, whereby a one-dimensional (1-d) signal at different aspect angles is graphically presented on any suitable display, such as an LCD (liquid crystal display), as a two-dimensional (2-d) image in terms of the cross-correlation coefficients and aspect angle. In addition, at step 140, the angular Mueller Matrix coefficients are expressed as analog signals, as shown in FIGS. 2a, whereupon the process continues to step 150. At step 150, the energy of the low frequency (large scale) and high frequency (small scale) wavelet components of the polarimetric signal at different aspect angles may be analyzed through scalogram analysis. Finally, at step 160 the power spectral density (PSD) of the received polarization signals is estimated using wavelet coefficients.

Thus, the present invention is enabled to present one-dimensional (1-d) polarimetric signals as two-dimensional (2-d) cross-correlation images with varying aspect angles.

Figure 15:
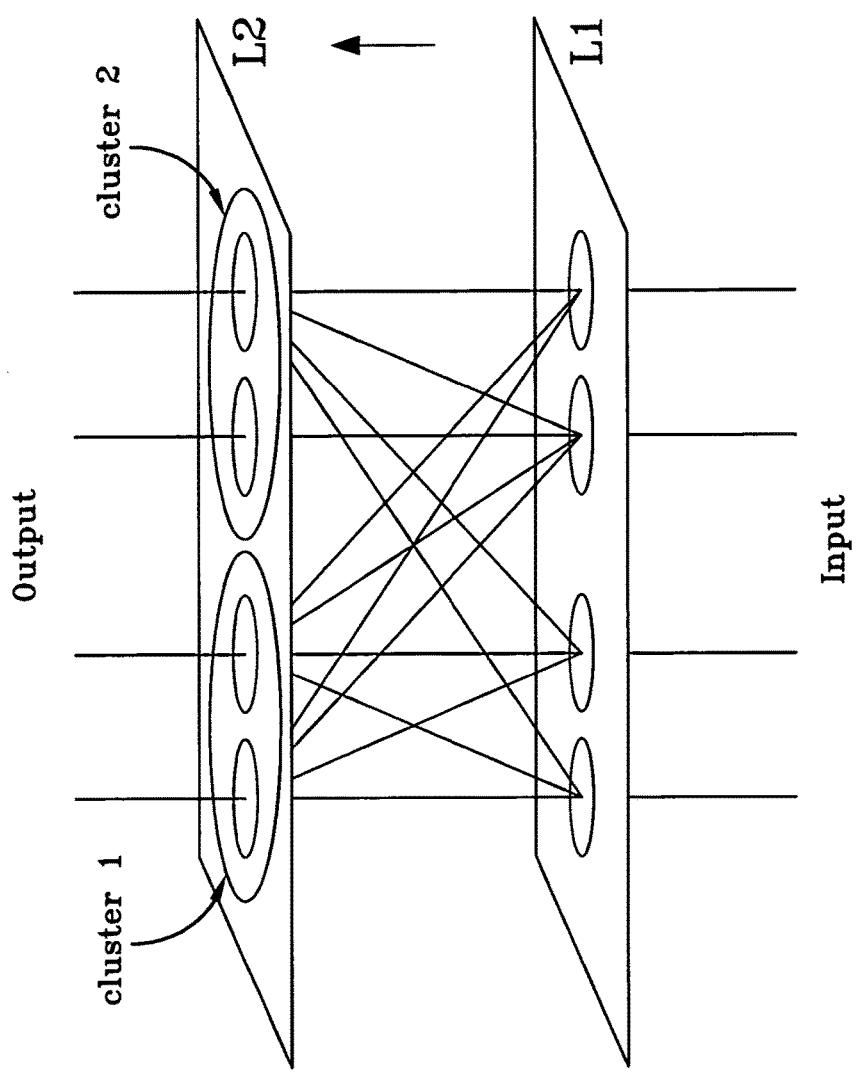
FIG. 15 is schematic view of a two-layered feed-forward network in accordance with the concepts of the present invention.

In addition, it is also contemplated that all the wavelet and fractal parameters, including the Mueller matrix elements, Stokes parameters, and statistical parameters are fed to a neural-fuzzy network for further optimization and image enhancement. For example, the Mueller matrix coefficients, Stokes parameters, wavelet coefficients, fractal dimensions, and correlation coefficients, power spectral density, and associated statistical parameters, may be input into a neural-fuzzy network for further optimization. This would lead to image enhancement with reduced false-alarm rate, and increased discrimination. One non-limiting example of the use of such optimization approach is that of an unsupervised two-layer feed-forward network (competitive learning), as shown in FIG. 15.

It should also be appreciated that the proposed invention may be utilized and applied to any system or technique capable of generating a Mueller matrix or Stokes parameter image, under active or passive illumination, transmission or backscattered geometry.

It should also be appreciated that the present invention is configured to detect and image any suitable target object or material, as well in a variety of applications, including but not limited to remote sensing, industrial applications, pharmaceutical applications, and biomedical/bio-analytical applications for example.

Experimental Evaluation

To evaluate and demonstrate the methodology of the process 100 of the present invention, two target materials comprising semiconductor materials are examined and imaged, namely, amorphous silicon and polycrystalline silicon (i.e. polysilicon). In addition, different cancer cells were also imaged using the process set forth by the present invention.

Figure 2:
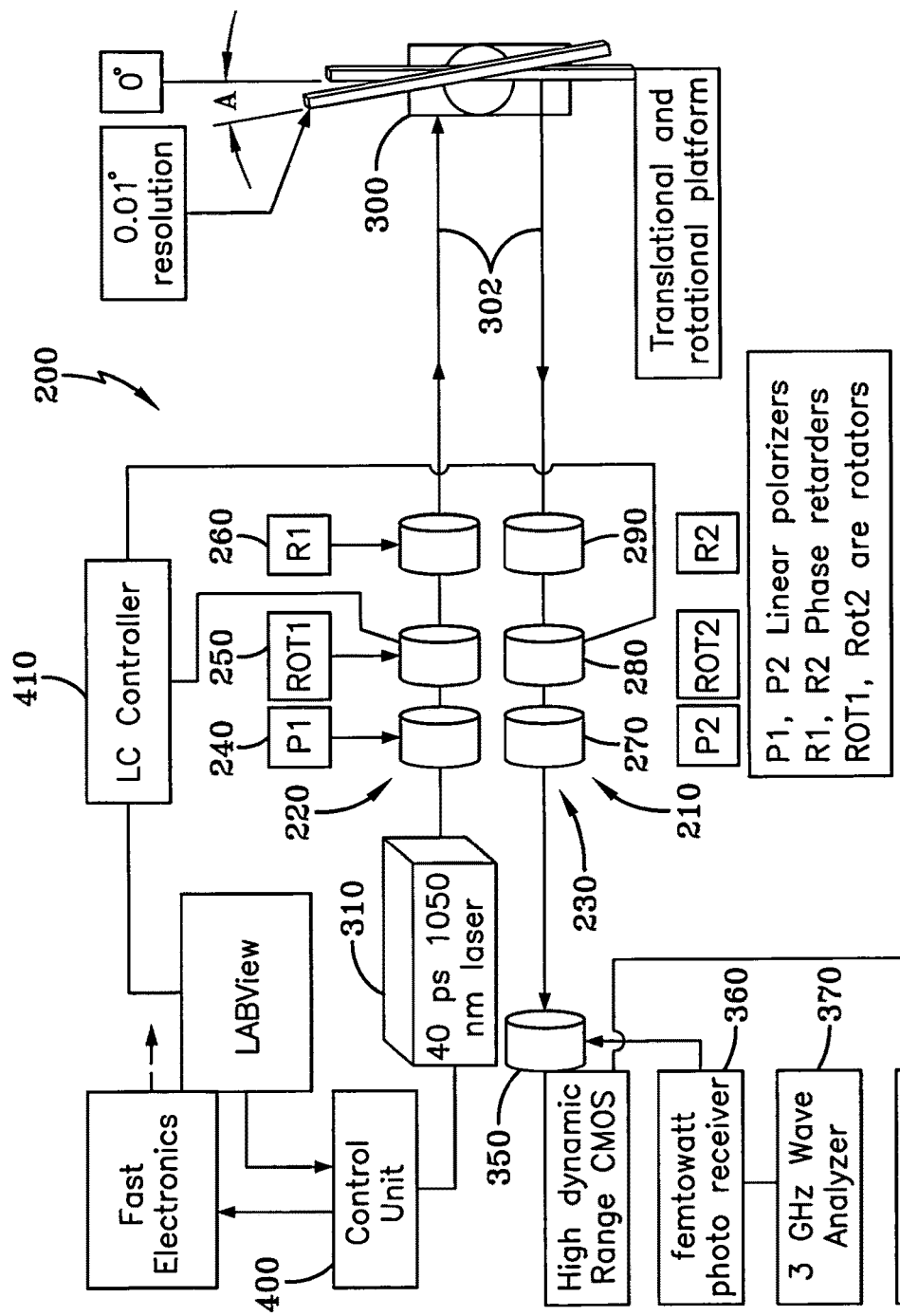
FIG. 2 is a schematic view of a polarimetric multifunctional imaging module used to perform the experimental analysis of the polarimetric wavelet detection system and method in accordance with the concepts of the present invention.

Continuing, a liquid crystal (LC) polarimetric multifunctional imaging module 200 used to study the polarimetric wavelet detection methodology of the present invention is shown in FIG. 2. In particular, the module 200 includes a liquid crystal unit 210 that provides transmission and reception optical units 220 and 230, whereby the transmission optical unit 220 includes an axially aligned linear polarizer 240 a rotator 250, and a phase retarder 260, while the reception optical unit 230 includes an axially aligned linear polarizer 270, a rotator 280, and a phase retarder 290. In optical alignment with the phase retarder 260 of the transmission optical unit 220 and the phase retarder 290 of the reception optical unit 230 is a translational and rotational platform 300. The platform 300 is configured to carry and rotate the target object/material thereon, such as the amorphous silicon and the polysilicon samples discussed herein, through various aspect angles during the imaging process. Moreover, the aspect angle, designated as 'A' in FIG. 2 is established by the position of the platform 300 relative to a laser beam 302 incident thereon. That is, the platform 300 is positioned so that it is normally substantially perpendicular to the laser beam 302 emitted by the laser source from the phase retarder 260. Thus, as the platform is rotated through each discrete aspect angle 'A', the surface of the platform 300 is oriented at an oblique angle (i.e. not perpendicular to the laser beam) to that of the laser beam 302 that is incident on the target object/material carried thereon that is being imaged. For example, the platform 300 may be rotated in any angle of desired angular resolution, such as 0.01° degrees for example. That is, the laser beam 302 is configured to pass through the transmission optical unit 220 whereupon the backscattered light passes through the reception optical unit 230.

A laser unit 310 is also in optical alignment with the linear polarizer 240 of the transmission optical unit 220. In one aspect the laser unit 310 may by configured to generate a 40 picosecond 1050 nm laser beam 302 for example. Furthermore, in optical communication with the linear polarizer 270 of the reception optical unit 230 is a high dynamic range CMOS (complementary metal oxide semiconductor) sensor 350 that is coupled to a femtowatt photoreceiver 360 for example that is configured to detect the backscattered polarimetric signals received from the target object/material. Coupled to the photoreceiver 350 is a wave analyzer 370, such as a 3 GHz wave analyzer for example, which is analyzed by a MATLAB-based software monitoring system.

The module 200 also includes a control unit 400 that includes the necessary hardware and software to carry out the functions to be discussed. In addition, the control unit 400 is coupled to a LC (liquid crystal) controller 410 and to the laser unit 310, such that the control unit 400 is interfaced with the LC controller 410 by a LABVIEW script module or other suitable interface program. In particular, the LC controller 410 is coupled to each of the rotators 250 and 280 to control their operation.

Figure 3:
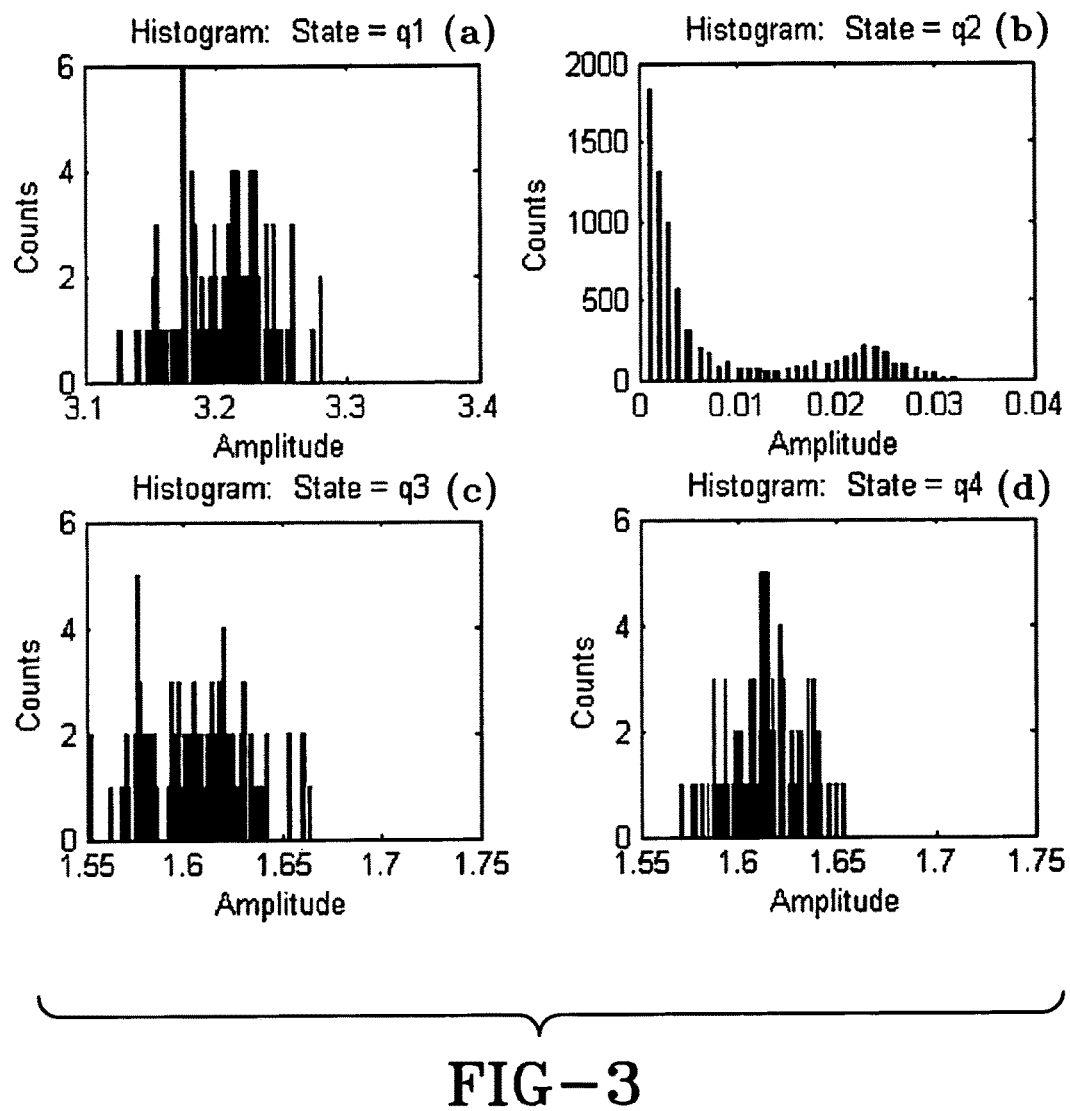
FIGS. 3a-d are histograms of the polarimetric states acquired during the calibration of the polarimetric multifunctional imaging module of FIG. 2 for states q=1, 2, 3, and 4 in accordance with the concepts of the present invention.
Figure 4:
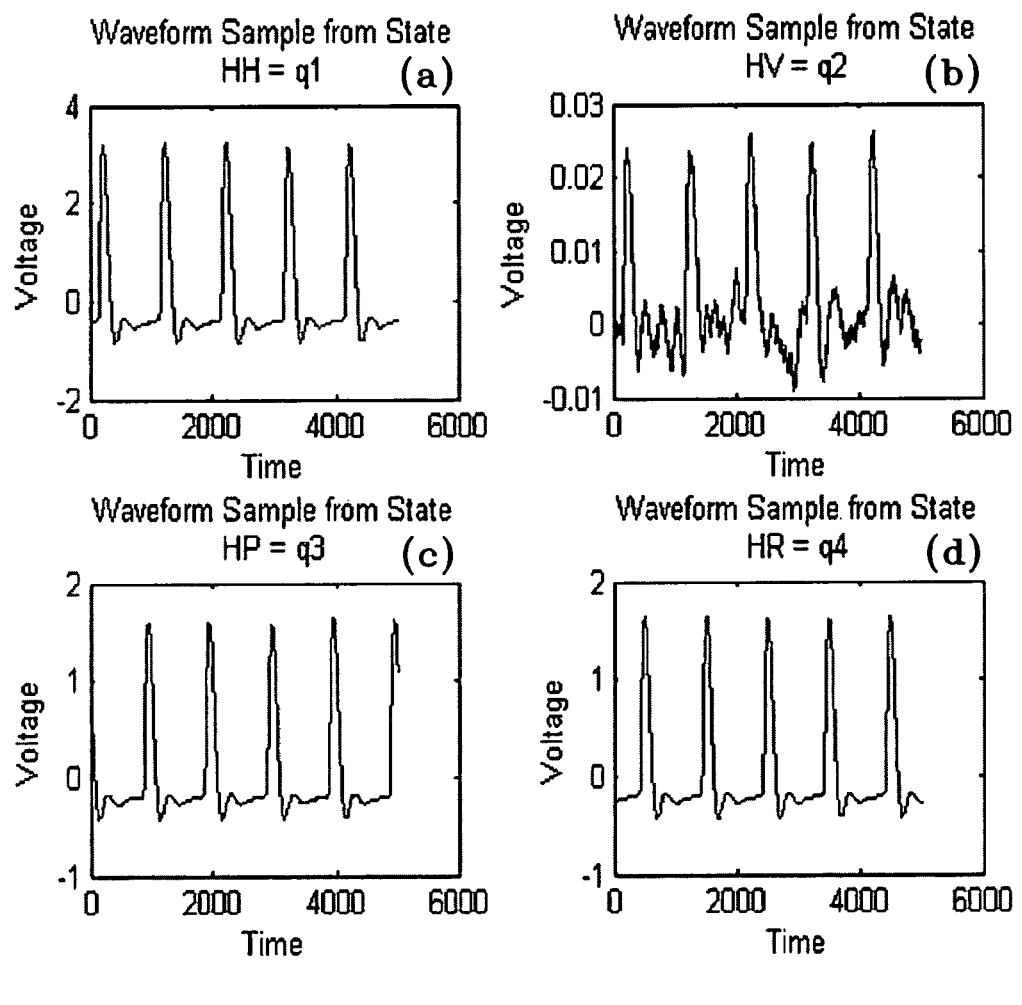
FIGS. 4a-d show one-dimensional time domain waveforms of the Mueller Matrix signals/elements acquired during calibration of the polarimetric multifunctional imaging module of FIG. 2 for states q=1, 2, 3, and 4 in accordance with the concepts of the present invention.

As such, the system 200 comprises a complete polarimeter capable of measuring the full 16 element 4×4 Mueller Matrix of a target object/material using the liquid crystal (LC) unit 210. The liquid crystal unit 210 allows full electronic control, and the system is highly automated. LABVIEW scripts were used to control the devices and measurement states and perform a detailed calibration of the optical system. As an example of the capabilities of the system 200, the acquired Mueller Matrix signals during calibration of the states q=1,2,3,4 are plotted both as histograms and Id time-domain signals in FIGS. 3 and 4, respectively.

Figure 5:
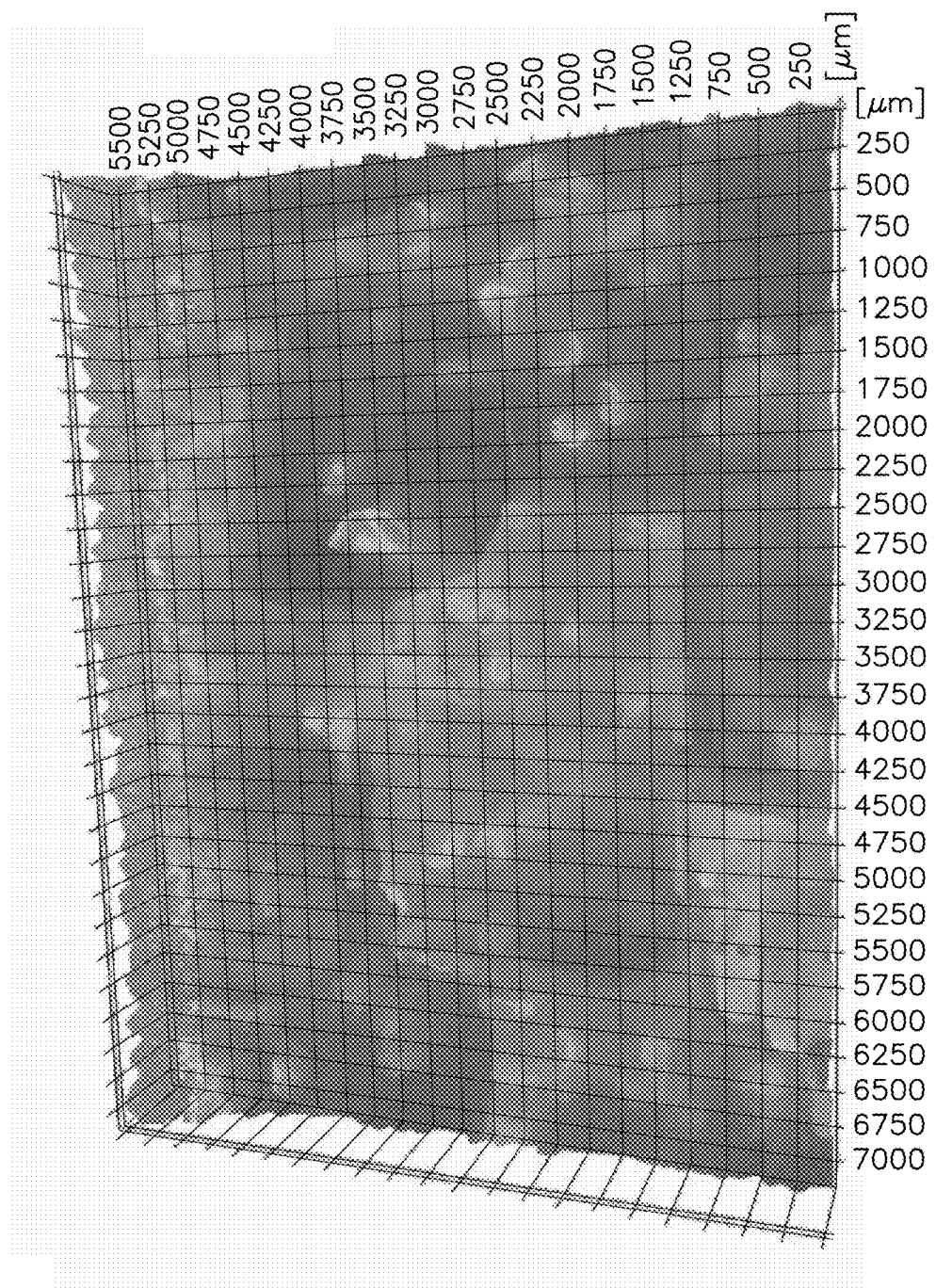
FIG. 5 is a confocal microscopy image of an amorphous silicon semiconductor sample that was obtained using the polarimetric wavelet detection system in accordance with the concepts of the present invention.
Figure 6:
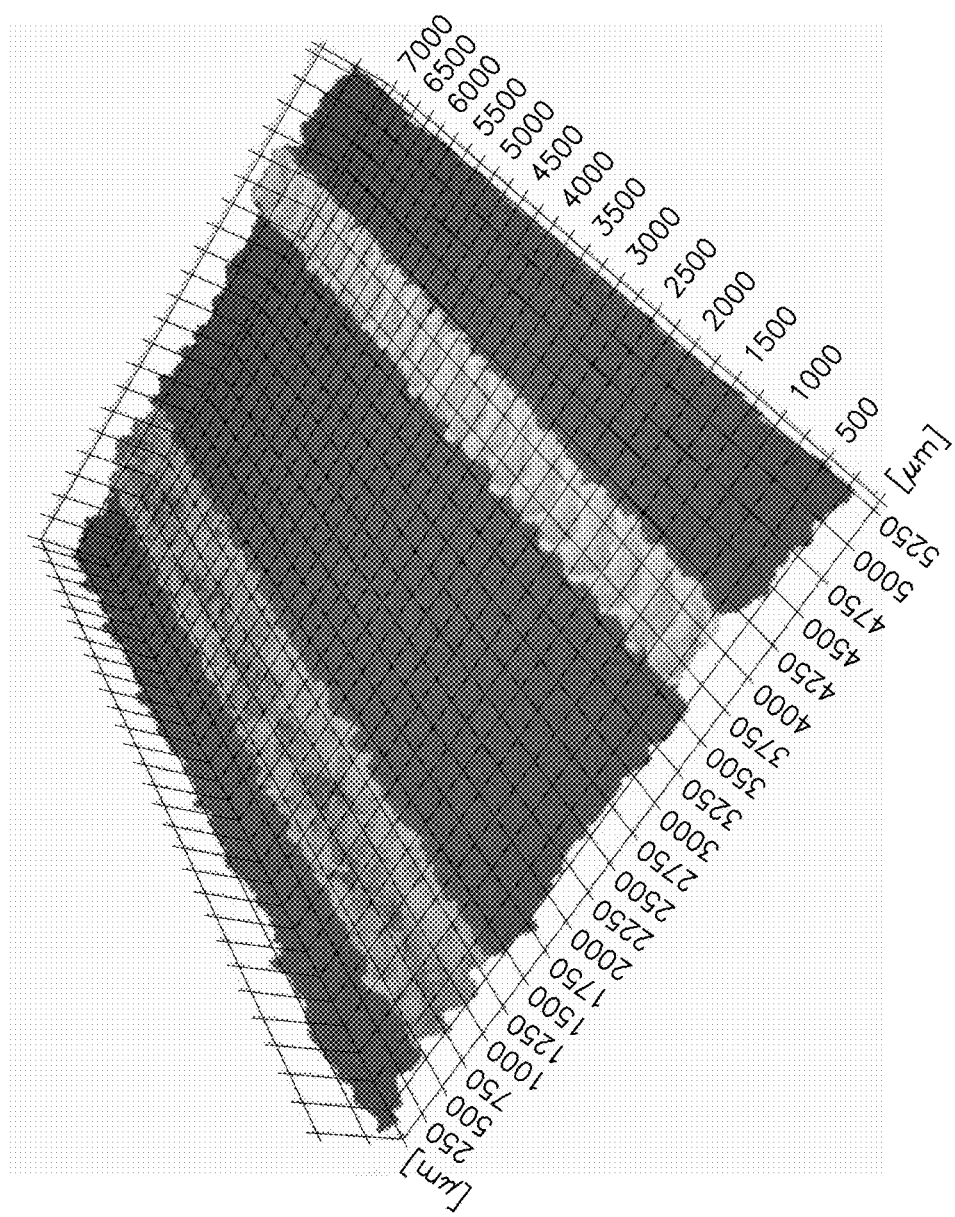
FIG. 6 is a confocal microscopy image of a polysilicon semiconductor sample that was obtained using the polarimetric wavelet detection system in accordance with the concepts of the present invention.

Confocal microscopy images for both amorphous silicon and polysilicon semiconductor samples were obtained and examples are shown in FIGS. 5 and 6, respectively. The amorphous silicon semiconductor sample has a characteristic size of approximately 2 mm, while the polysilicon semiconductor sample has grain sizes in the micrometer range. This explains the enhanced specular characteristics associated with amorphous silicon rather than polysilicon, which exhibits pronounced diffuse scattering.

Figure 7:
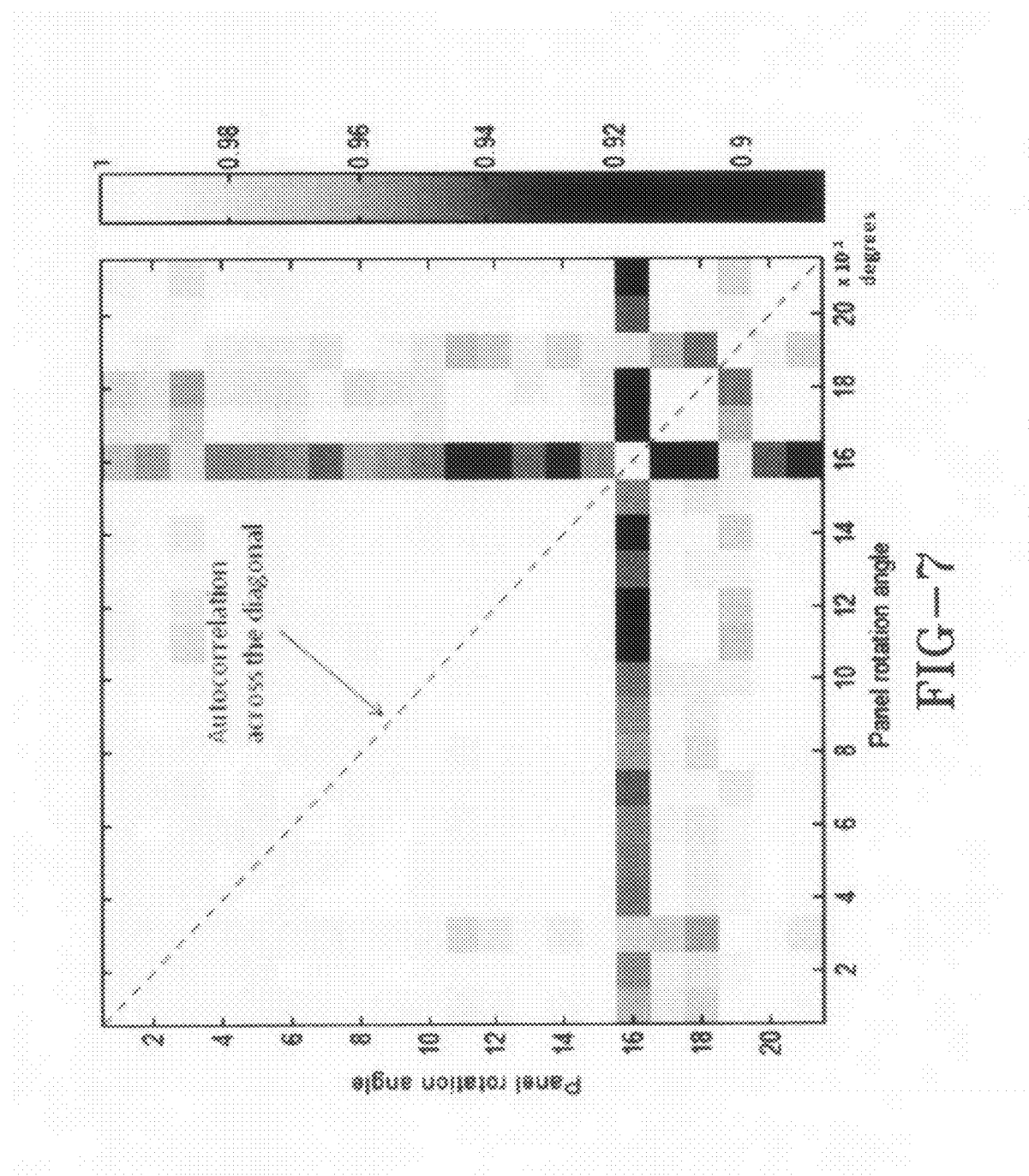
FIG. 7 is a graphical representation of the cross-correlation between backscattered polarimetric signals at different aspect angles for an amorphous silicon-based semiconductor sample in accordance with the concepts of the present invention.
Figure 8:
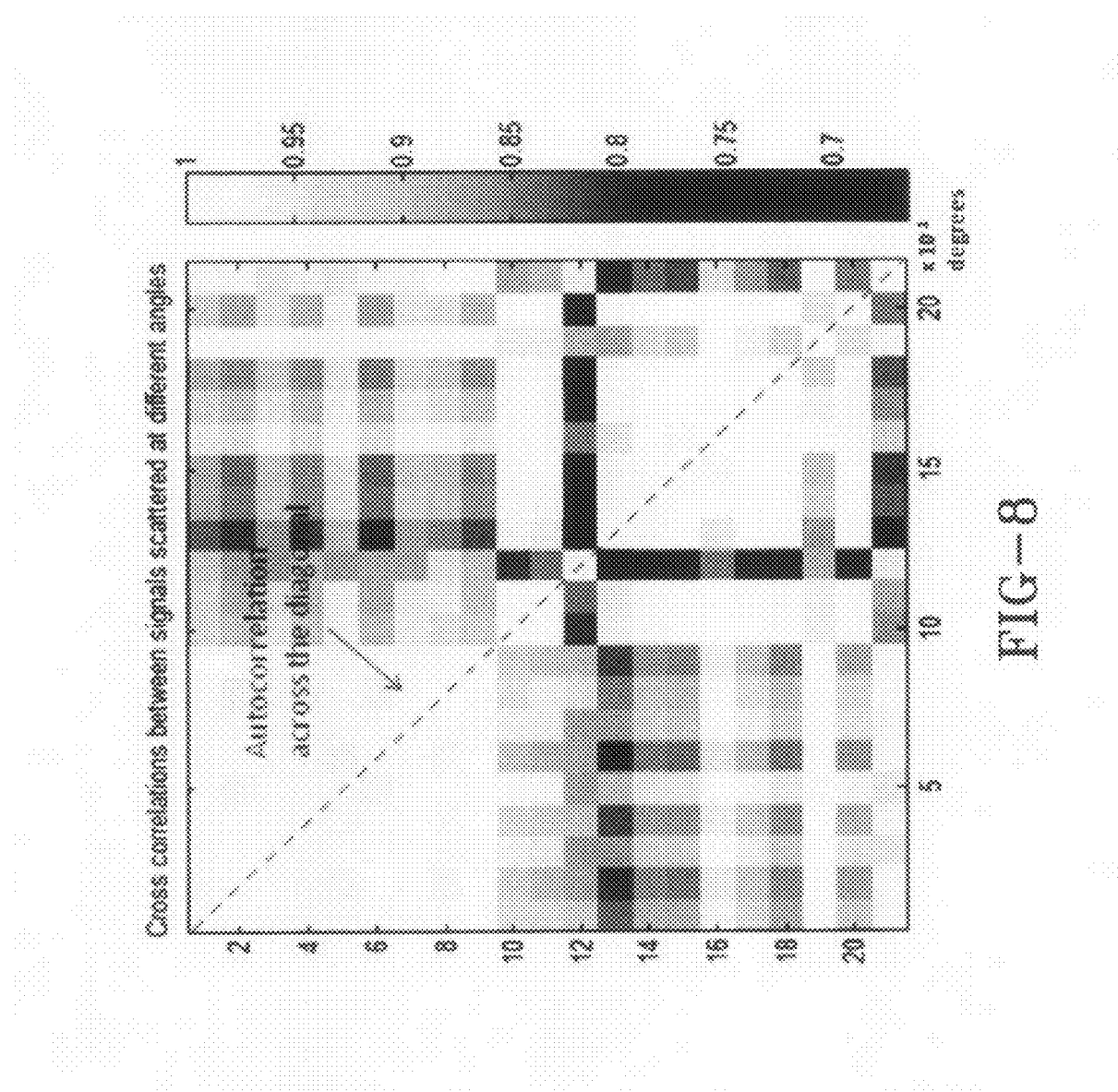
FIG. 8 is a graphical representation of the cross-correlation between backscattered polarimetric signals at different aspect angles for a polysilicon-based semiconductor sample in accordance with the concepts of the present invention.

Polarimetric signal similarity is quantified in terms of the correlation coefficients of the polarimetric signals obtained at different aspect angles of the target silicon material samples. A pictorial representation of the cross-correlations between the backscattered polarimetric signals from amorphous silicon and polysilicon-based semiconductor samples, at varying aspect angles, are shown in FIGS. 7 and 8, respectively. The x and y axes of the graphs of FIGS. 7 and 8 represent the aspect angle values, such that the number 1 is the least aspect angle, representing 0 degrees, and number 21 is the highest aspect angle, representing 2 degrees, while the remaining aspect angles are linearly and uniformly distributed between these limits from 0 to 21. As a result, the whiter (i.e. lighter) regions or pixels of FIGS. 7 and 8 represent high correlations and large amplitudes.

Each pixel value in FIGS. 7 and 8 represents the correlation coefficients between backscattered polarimetric signals recorded at the corresponding aspect angles. In the diagrams, white (i.e. lightest) regions or pixels represents a value of 1 (white) indicating a 100% likeness, while progressively darker pixel shades indicate a proportionally reduced degree of likeness. By observing FIGS. 7 and 8, it is apparent that amorphous silicon exhibits more signal similarity (whiter regions) than polysilicon within certain regions of interest (ROI). However, polysilicon reveals a pronounced periodicity of alternating similar (whiter/lighter) and dissimilar (darker) structures within the same ROI. A decreased correlation would be attributed to signal distortion that is caused by interaction of the laser beam with the semiconductor sample structures or patterns. A pronounced decrease in correlation is observed in the immediate area of the specular reflection direction for the polysilicon (FIG. 8) semiconductor sample (1.2°), at x-y values of 12 (corresponding to 1.1°). Likewise, a correlation decrease is observed at x-y values of 16 (1.5°) for the amorphous silicon semiconductor sample (FIG. 7), where an increased intensity of the polarimetric signal is observed.

Figure 9A:
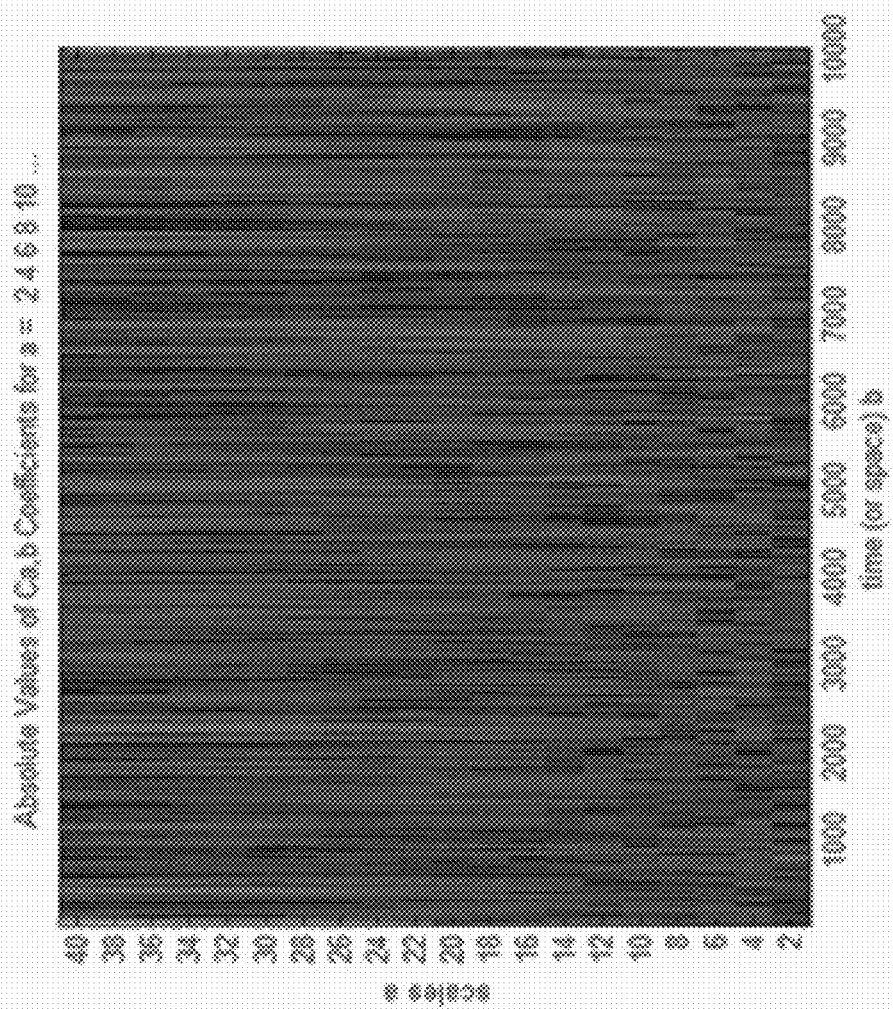
FIGS. 9a-d are scalograms acquired at an aspect angle of 0.1° for amorphous silicon semiconductor samples (FIGS. 9a-b) and for polysilicon semiconductor samples (FIGS. 9c-d) in accordance with the concepts of the present invention.
Figure 9B:
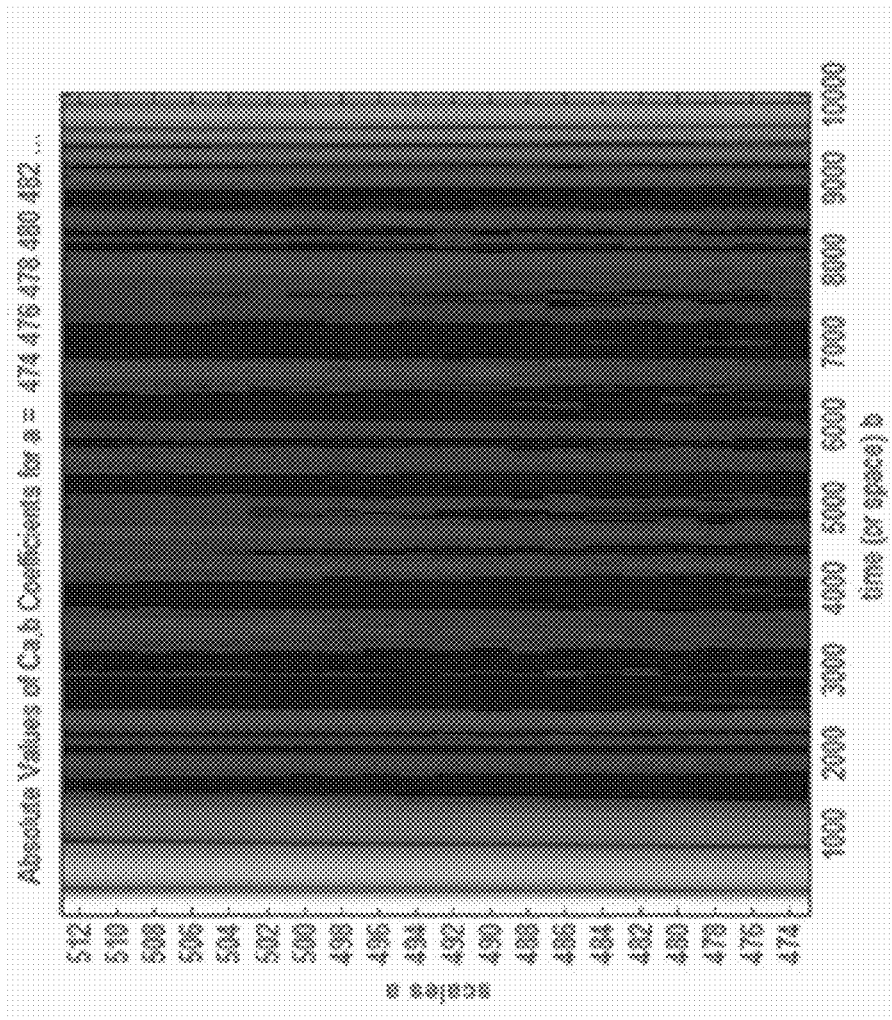
Figure 9C:
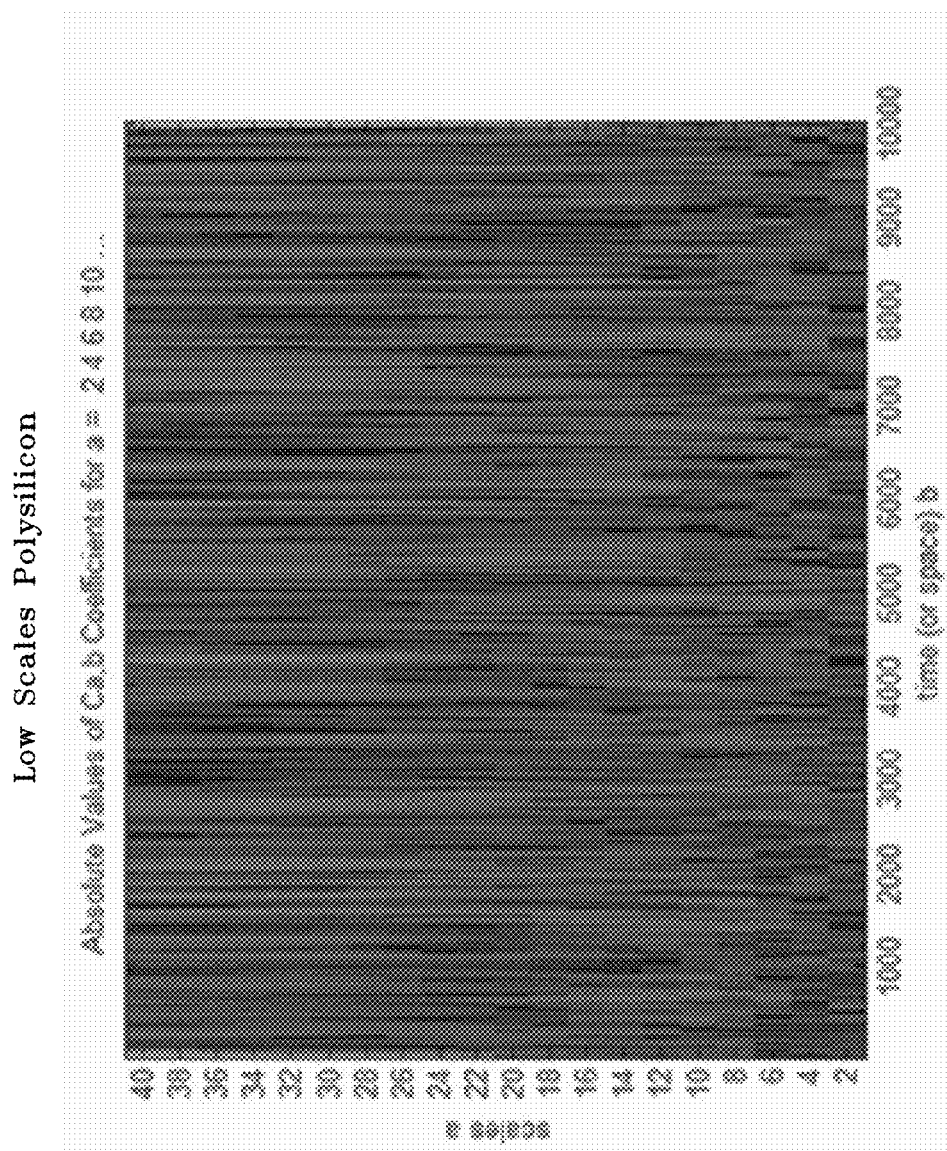
Figure 9D:
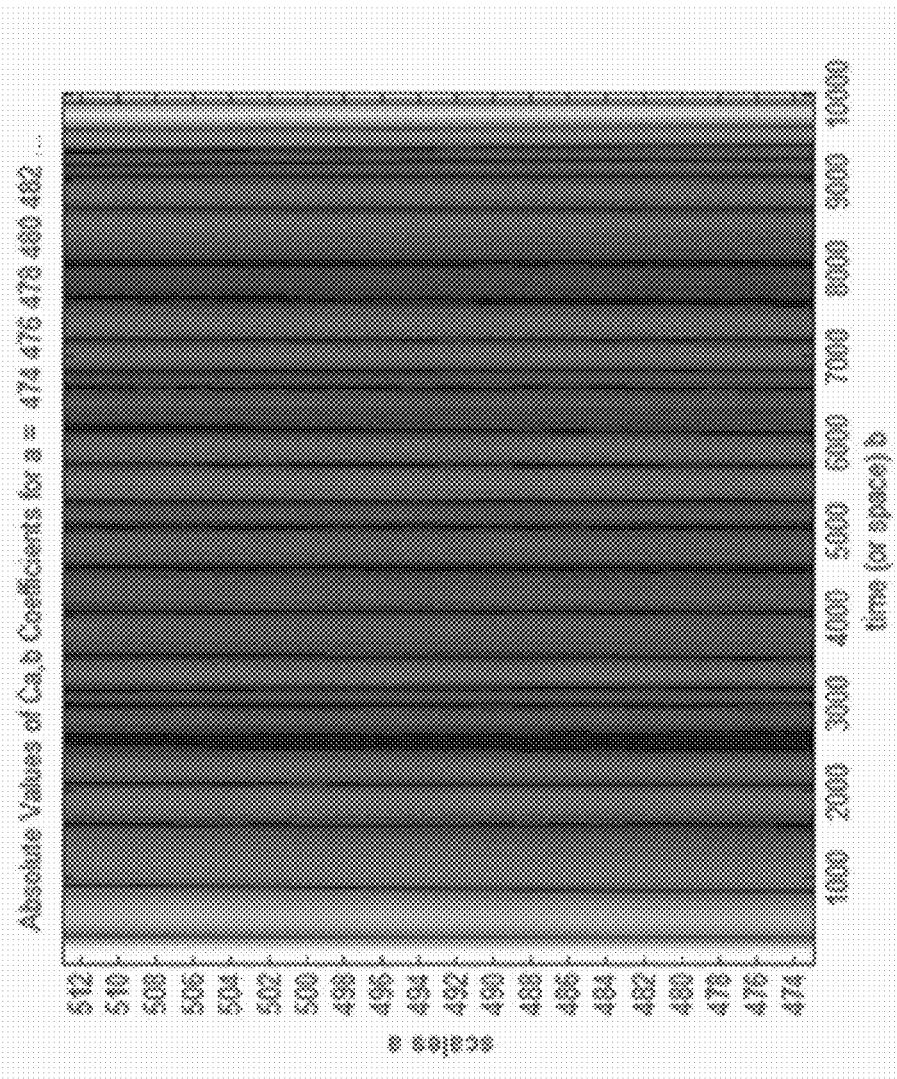

Analysis of the acquired polarimetric backscattered polarization state signals or waveforms was then performed using wavelet transforms. In this analysis, the particular wavelet was chosen from the Daubechies family, namely, the 'db4' wavelet, although any wavelet can be applied, for different scenarios. Scalograms were calculated for an aspect angle ranging from 0 to 2 degrees. FIGS. 9A-B show examples of scalograms obtained for amorphous silicon semiconductor samples, and FIGS. 9C-D show examples of scalograms obtained for polysilicon semiconductor samples. Upon calculation of the scalogram coefficients, the energy in the lower and upper frequency bands of the backscattered polarimetric signal were calculated. Specifically, 20 scale values are included and used to define the upper and lower bands of the scalogram. The lower (i.e. smaller) scales correspond to high frequency components of the backscattered polarimetric signal, and the higher (i.e. larger) scales correspond to low frequency components of the backscattered polarimetric signal.

Figure 10:
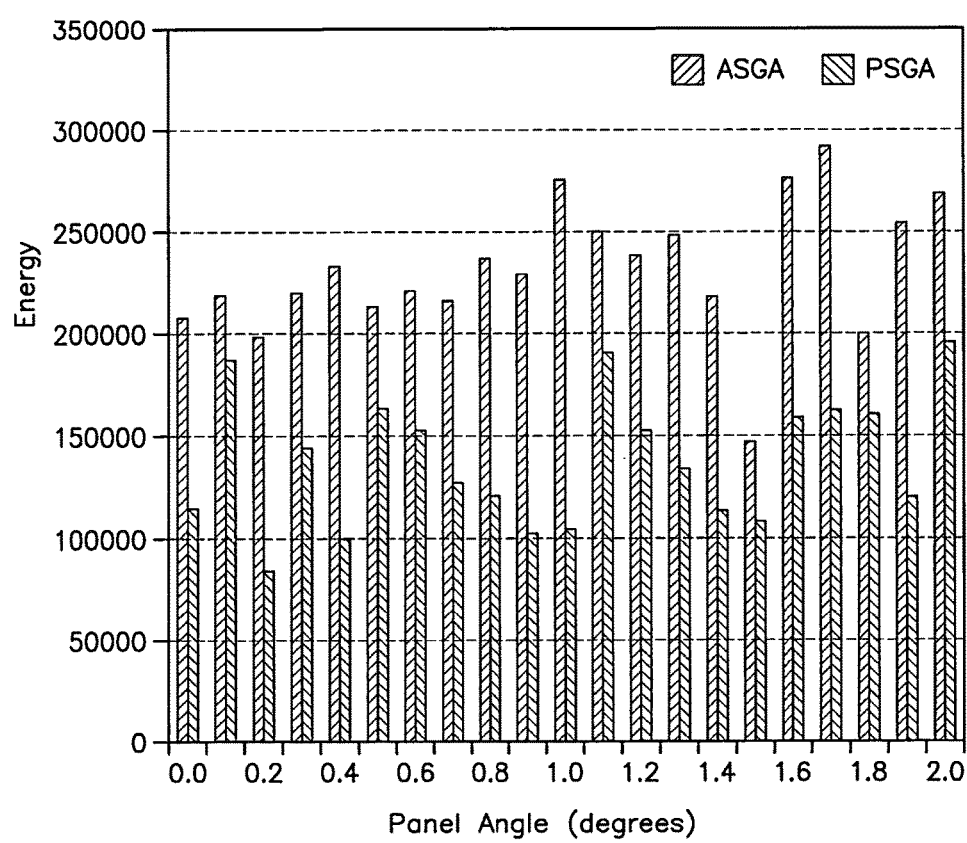
FIG. 10 is a chart showing the total energy versus aspect angle for the amorphous silicon semiconductor sample, designated as "ASGA", and for the polysilicon semiconductor cell sample, designated as "PSGA", in accordance with the concepts of the present invention.
Figure 11A:
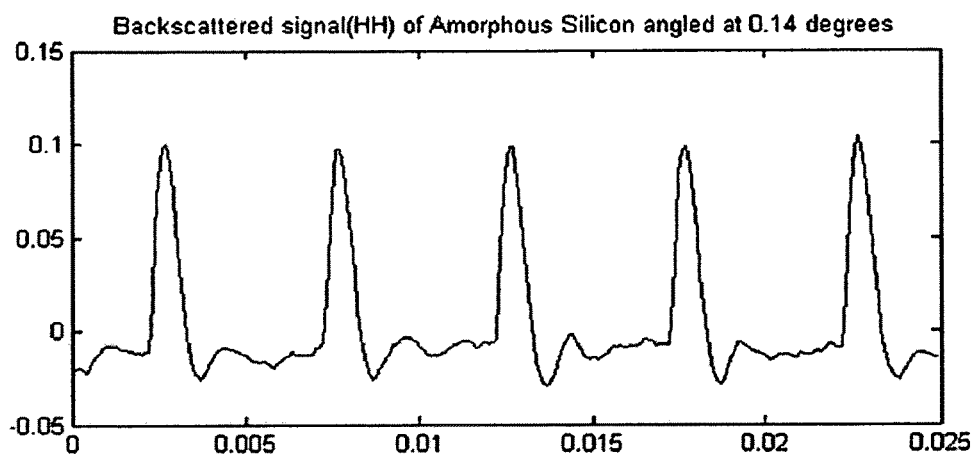
FIGS. 11a-d are graphs of backscattered signals HH and HV of amorphous silicon in accordance with the concepts of the present invention.
Figure 11B:
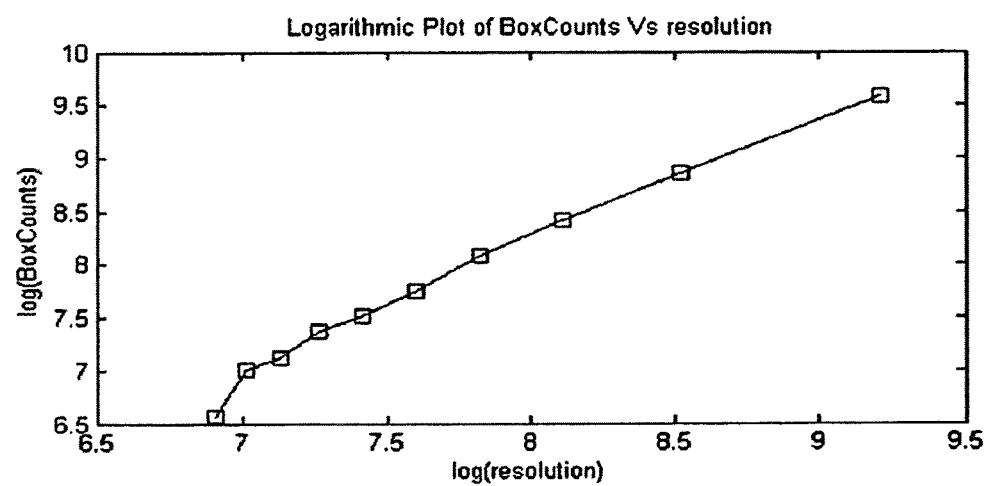
Figure 11C:
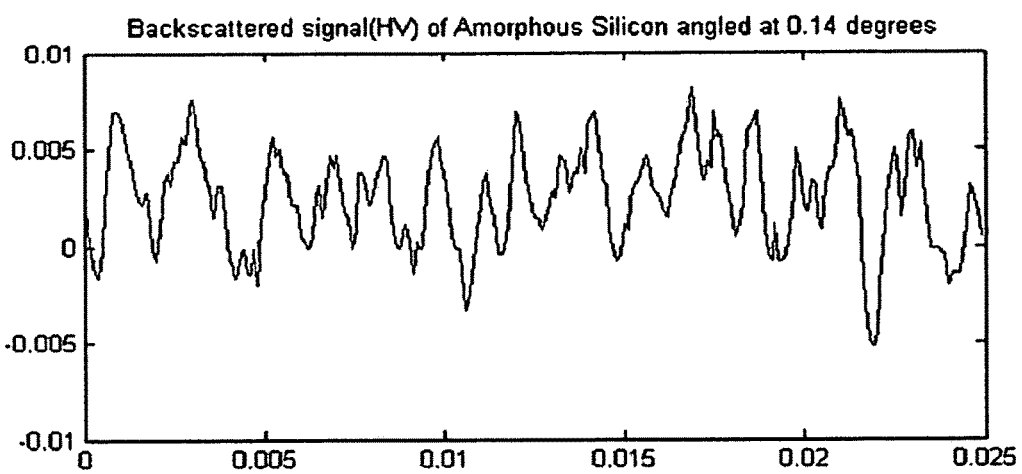
Figure 11D:
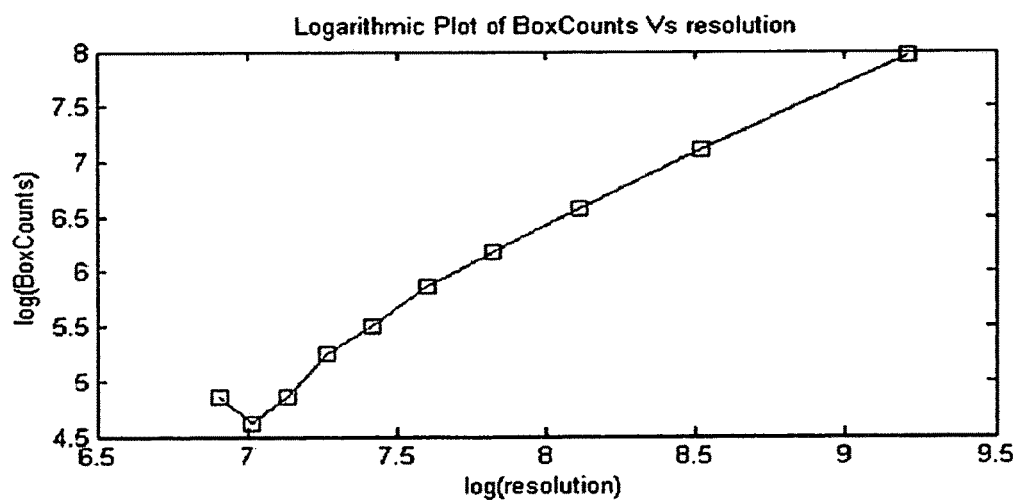

The total energy versus aspect angle is shown in the chart of FIG. 10. The acquired polarimetric waveforms at different aspect angles were not sequential, but rather separated by an arbitrary time interval of approximately 10-15 minutes. It is observed from FIG. 10 that more laser power was returned by the amorphous silicon sample as compared to the polysilicon sample, an observation confirmed through further experimental studies. This can be interpreted based on the higher specular reflection characteristics of amorphous silicon as compared to polysilicon, which exhibits rather pronounced diffuse reflectance because of the micron sized discrete grains. Indeed, there is a pronounced periodicity in the energy levels associated with the polysilicon semiconductor sample. In addition, the correlation image of FIG. 8 for the polysilicon material also reveals a pronounced periodic structure (as discussed earlier). The prevalence of the low-frequency components on both materials is directly related to the low laser modulation frequency, which make wavelet applications suitable in this scenario for enhanced frequency resolution rather than for time localization.

In FIG. 9, an improved version of the box dimension method, namely the "Multiresolution Box-counting Method" was used. The applied technique estimates the fractal dimension with less computational time and is insensitive to wave amplitude, therefore providing enhanced robustness for real-time applications.

Figure 12:
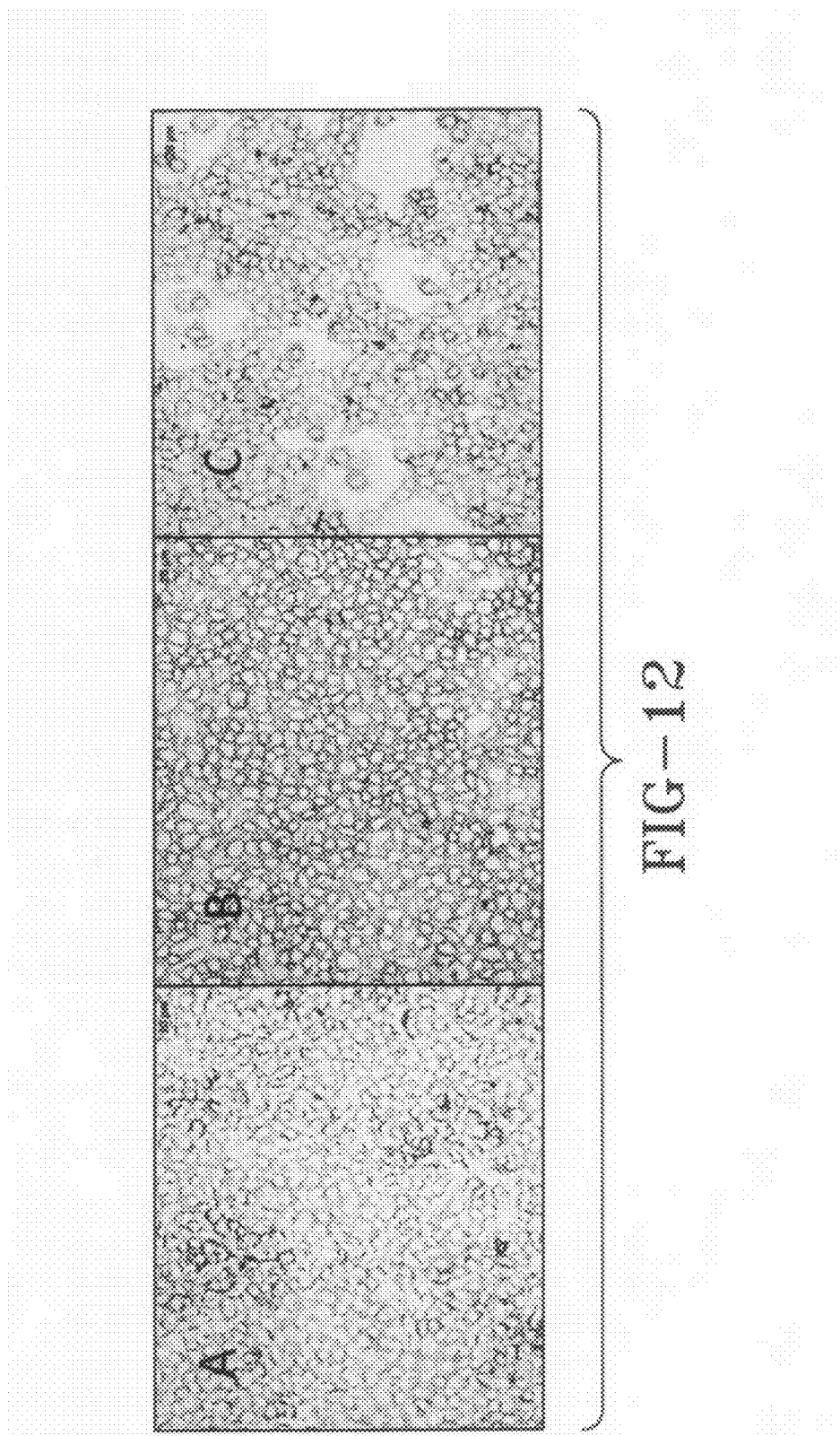
FIGS. 12a-c are confocal images of stage II squamous carcinoma, stage II adenocarcinoma; and a mixture of stage II squamous carcinoma and stage II adenocarcinoma.
Figure 13A:
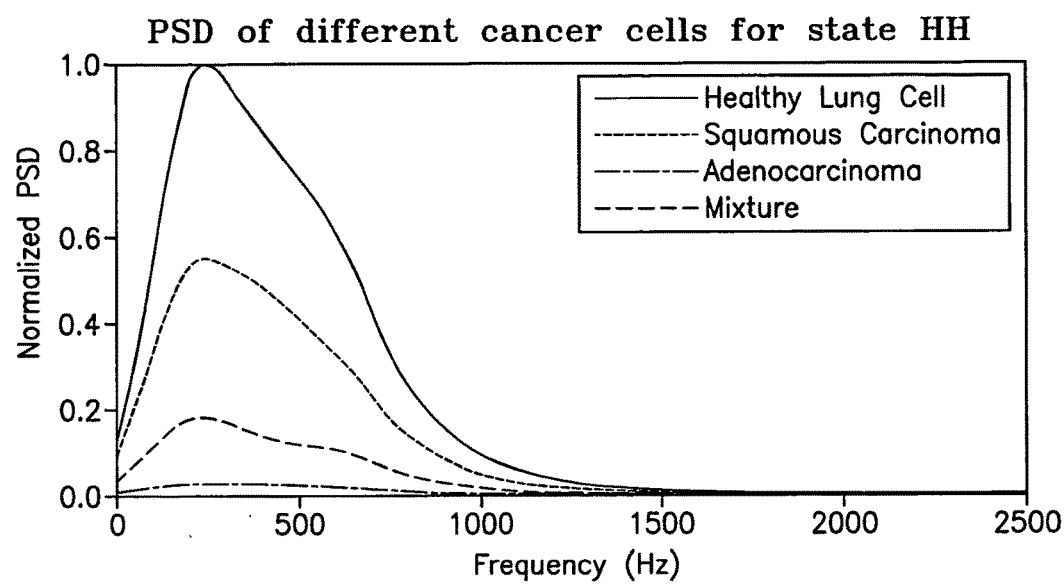
FIGS. 13a-d are charts showing the spectrum power calculated for different measurement states (HH, HV, VP, and HR) in accordance with the concepts of the present invention.
Figure 13B:
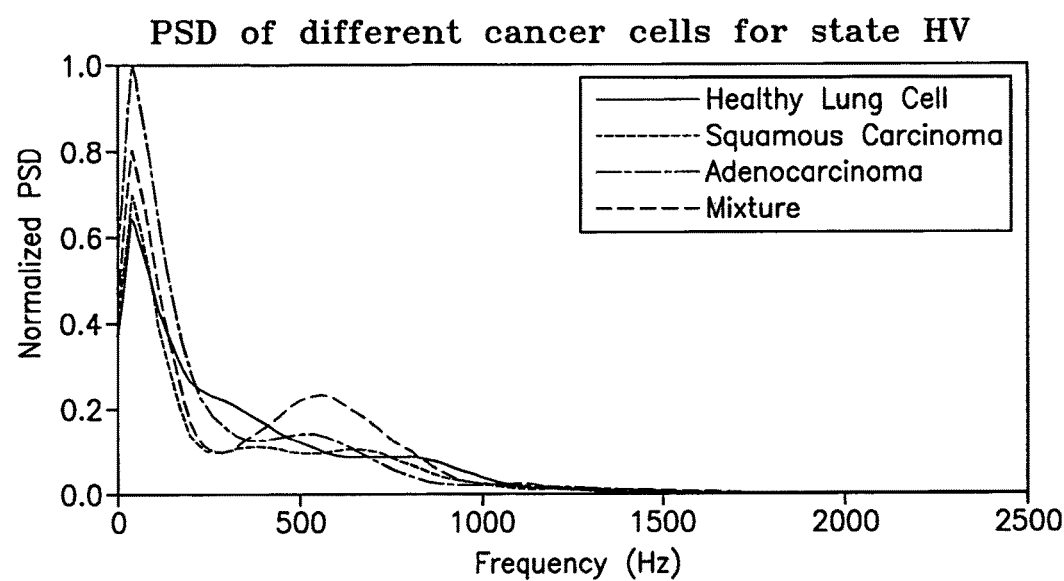
Figure 13C:
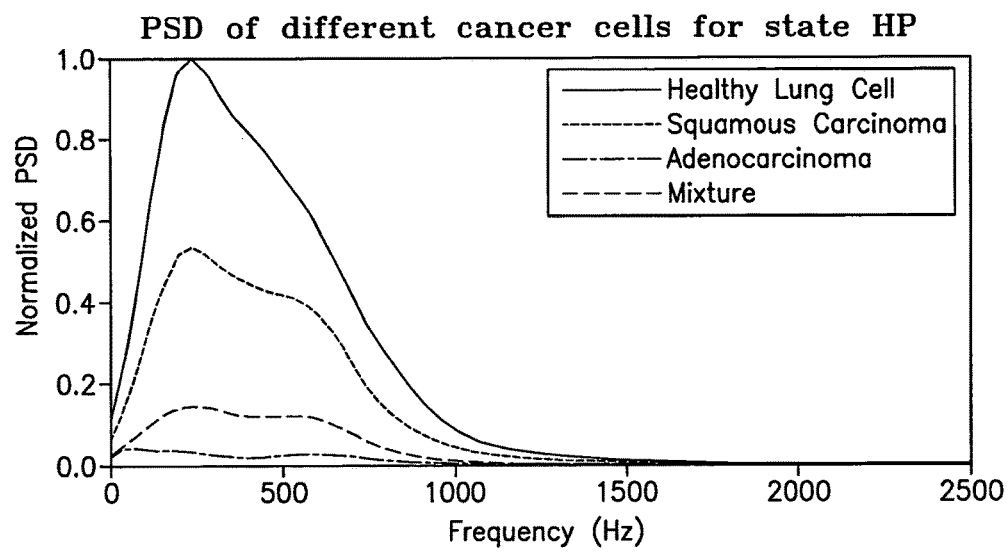
Figure 13D:
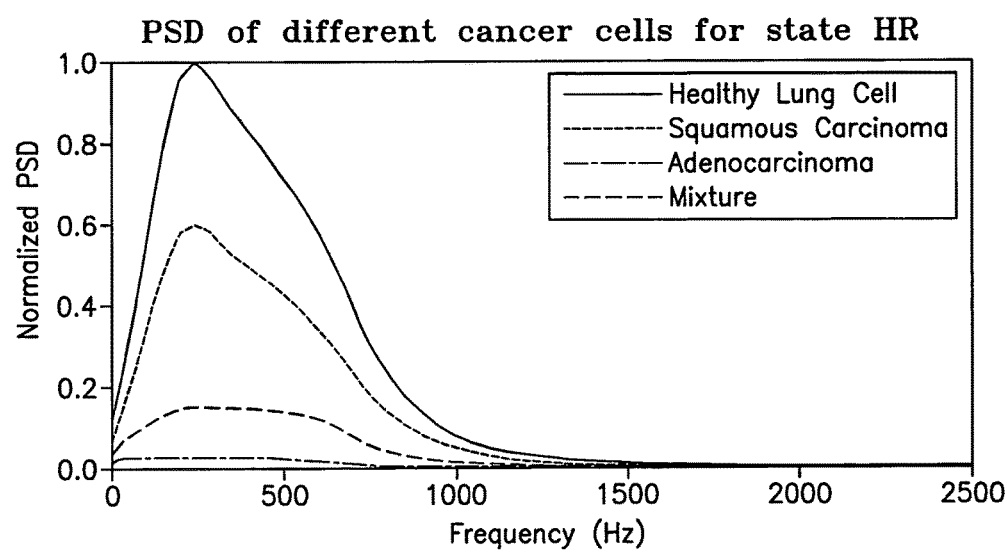
Figure 14:
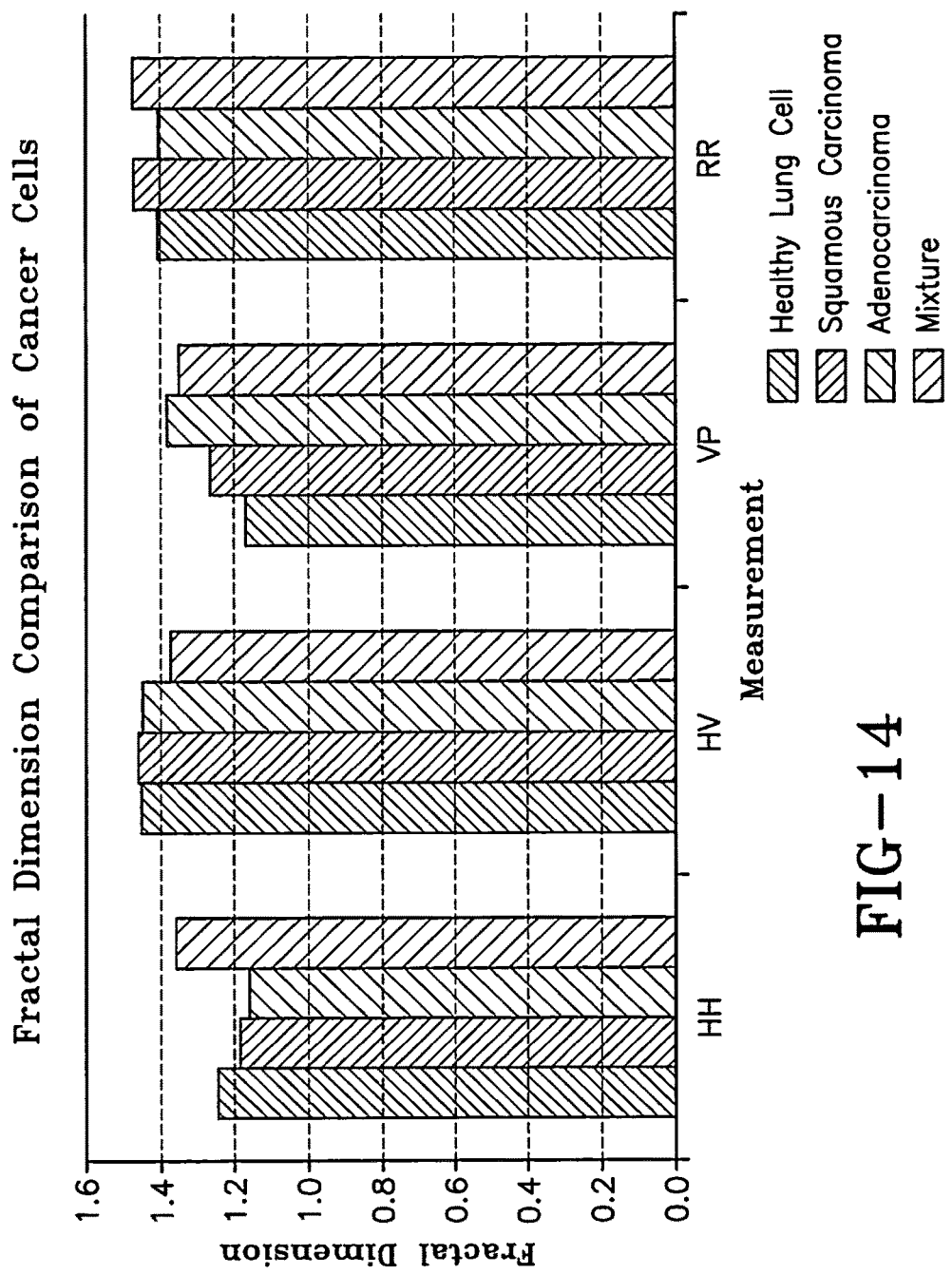
FIG. 14 is a chart showing the fractal dimension of cancer cells at different measurement states, in accordance with the concepts of the present invention.

With regard to the imaging of cancer cells using the present invention, FIGS. 11a-d show graphs of backscattered signals HH and HV of amorphous silicon in accordance with the concepts of the present invention. In addition, FIGS. 12a-c are confocal images of stage II squamous carcinoma, stage II adenocarcinoma; and a mixture of stage II squamous carcinoma and stage II adenocarcinoma. FIGS. 13a-d are charts showing the spectrum power analysis for cancer cells using the present invention that were calculated for different measurement states (HH, HV, VP, and HR). FIG. 14 is a chart showing the fractal dimension of cancer cells image by the present invention at different measurement states. Finally, FIG. 15 is schematic view of a two-layered feed-forward network in accordance with the concepts of the present invention.

Thus, the present invention provides a remote sensing system and method that is based on the correlation and fractal wavelet analyses of polarimetric signals. As such, the results presented for two semiconductor samples of amorphous and polysilicon materials supports remote characterization of a target object/material, such as space materials and structures, with enhanced discrimination, localization, and high-dynamic range while maintaining optimized sensitivity.

Therefore, one advantage of the present invention is that a system and method for polarimetric fractal wavelet detection of a target object/material is applied on an angular Mueller Matrix or Stokes parameters image, allowing characterization of the target object/material to be carried out to achieve enhanced discrimination, localization, and high-dynamic range, while maintaining optimal sensitivity. Still another advantage of the present invention is that a system and method for polarimetric wavelet detection is configured to combine power spectral density (PSD), cross-correlation of the polarimetric signals and fractal wavelet principles at different aspect angles to achieve enhanced detection and discrimination of target objects/materials, such as space materials.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A method for imaging a target object illuminated by a light source at a plurality of aspect angles, the method comprising: generating an angular Mueller Matrix for each one of the aspect angles measured using the light source, said Mueller Matrix having a plurality of matrix elements each representing a polarimetric state of the target object at one of the aspect angles, said matrix elements being expressed as an analog signal; generating a Stokes vector for each one of the plurality of aspect angles, wherein said Stokes vector includes a plurality of vector elements; representing each one of said plurality of matrix elements and each one of said vector elements as a wavelet element; identifying a low frequency component and a high frequency component of each said wavelet element; estimating a power spectral density from said high and low frequency components; estimating a fractal dimension of said wavelet elements of each said Mueller Matrix and each said Stokes vector; generating a cross-correlation based on a polarimetric state of each said Mueller Matrix; and displaying a two-dimensional image of the target object based on said power spectral density, said wavelet elements, said cross-correlation, and said fractal dimension.

2. The method of claim 1, wherein the light source is active or passive.

3. The method of claim 1, wherein the light source is under transmission or backscattered geometry.

4. The method of claim 1, wherein said representing step is performed by a continuous wavelet transform.

5. The method of claim 4, wherein said continuous wavelet transform comprises a Daubechies wavelet transform.

6. The method of claim 1, wherein said fractal dimension is estimated by a method selected from the group consisting of: a box counting method, a multi-resolution box-counting method, a Katz method, a Sevcik method, a Higuhi method, a regularization method, or a maximum entropy method.

7. A method for imaging a target object illuminated by a light source at a plurality of aspect angles, the method comprising: generating an angular Mueller Matrix for each one of the aspect angles measured using the light source, said Mueller Matrix having a plurality of matrix elements each representing a polarimetric state of the target object at one of the aspect angles, said matrix elements being expressed as an analog signal; representing said matrix elements as respective wavelet elements; identifying a low frequency component and a high frequency component of said wavelet elements; estimating a power spectral density from said high and low frequency components; estimating a fractal dimension of said wavelet elements of each said Mueller Matrix; generating a cross-correlation based on a polarimetric state of each said Mueller Matrix; and displaying an image of the target object based on said power spectral density, said wavelet elements, said cross-correlation, and said fractal dimension.

8. The method of claim 7, wherein the light source is active or passive.

9. The method of claim 7, wherein the light source is under transmission or backscattered geometry.

10. The method of claim 7, further comprising:
optimizing said displaying step by processing said power spectral density and said fractal dimension through a neural-fuzzy network.

11. The method of claim 10, wherein said neural-fuzzy network comprises a two-layer feed-forward network.

12. The method of claim 7, wherein said continuous wavelet transform comprises a Daubechies wavelet transform.

13. The method of claim 7, wherein said fractal dimension is estimated by a method selected from the group consisting of: a box counting method, a multi-resolution box-counting method, a Katz method, a Sevcik method, a Higuhi method, a regularization method, or a maximum entropy method.

* * * * *